United States Patent
Nagase et al.

(10) Patent No.: US 8,063,238 B2
(45) Date of Patent: Nov. 22, 2011

(54) DIAMINE COMPOUND HAVING PHOSPHORYLCHOLINE GROUP, POLYMER THEREOF, AND PROCESS FOR PRODUCING THE POLYMER

(75) Inventors: Yu Nagase, Hiratsuka (JP); Naoya Shimoyamada, Hiratsuka (JP); Yasuhiko Iwasaki, Tokyo (JP); Kazuhiko Ishihara, Mitaka (JP)

(73) Assignees: Tokai University Educational System, Tokyo (JP); Tokyo Medical and Dental University, Tokyo (JP)

( * ) Notice: Subject to any disclaimer, the term of this patent is extended or adjusted under 35 U.S.C. 154(b) by 357 days.

(21) Appl. No.: 12/439,192

(22) PCT Filed: Aug. 31, 2007

(86) PCT No.: PCT/JP2007/067061
§ 371 (c)(1),
(2), (4) Date: Feb. 27, 2009

(87) PCT Pub. No.: WO2008/029744
PCT Pub. Date: Mar. 13, 2008

(65) Prior Publication Data
US 2010/0036081 A1     Feb. 11, 2010

(30) Foreign Application Priority Data

Sep. 1, 2006   (JP) ................. 2006-237802
Feb. 16, 2007  (JP) ................. 2007-036552

(51) Int. Cl.
C07F 9/02       (2006.01)
C08G 18/70      (2006.01)
(52) U.S. Cl. ......................... 558/169; 528/72
(58) Field of Classification Search .......... 558/169; 528/72
See application file for complete search history.

(56) References Cited

U.S. PATENT DOCUMENTS
7,378,538 B2   5/2008  Nagase et al.

FOREIGN PATENT DOCUMENTS
| JP | 8000723 A | 1/1996 |
| JP | 10176021 A | 6/1998 |
| JP | 2001302598 A | 10/2001 |
| JP | 2001302745 A | 10/2001 |
| JP | 2002069178 A | 3/2002 |
| WO | 2004074298 A1 | 9/2004 |

OTHER PUBLICATIONS

Kazuhiko Ishihara et al., "Preparation of Phospholipid Polymers and Their Properties as Polymer Hydrogel Membranes", Polymer Journal, 1990, pp. 355-360, vol. 22, No. 5.

Kazuhiko Ishihara et al., "New development of antithrombogenic materials", Geka (Surgery), 1999, pp. 132-135 vol. 61, No. 2, plus English-language translation (3 pp.).

*Primary Examiner* — Rei-tsang Shiao
(74) *Attorney, Agent, or Firm* — The Webb Law Firm

(57) ABSTRACT

Highly polymerizable diamine compounds having a phosphorylcholine group are disclosed. High-molecular weight polymers are obtained from the highly polymerizable diamine compound having a phosphorylcholine group as a monomer, and the polymers have improved mechanical strength, water resistance and heat resistance while maintaining excellent biocompatibility and processability of MPC polymers. Processes for producing the polymers are disclosed. The diamine compounds having a phosphorylcholine group are represented by Formula (I). The polymers contain at least 1 mol % of a specific structural unit with a phosphorylcholine group represented by Formula (II) and have a number average molecular weight of not less than 5,000. In the processes, the diamine compound is used as a monomer.

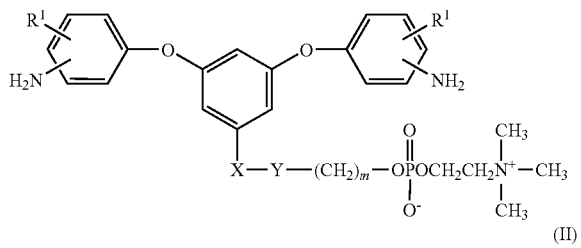

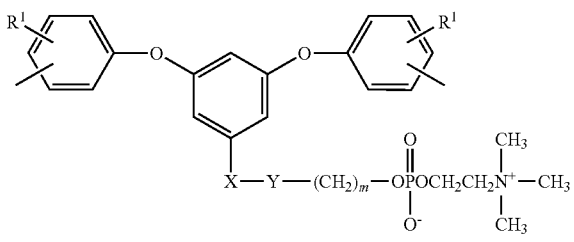

9 Claims, 1 Drawing Sheet

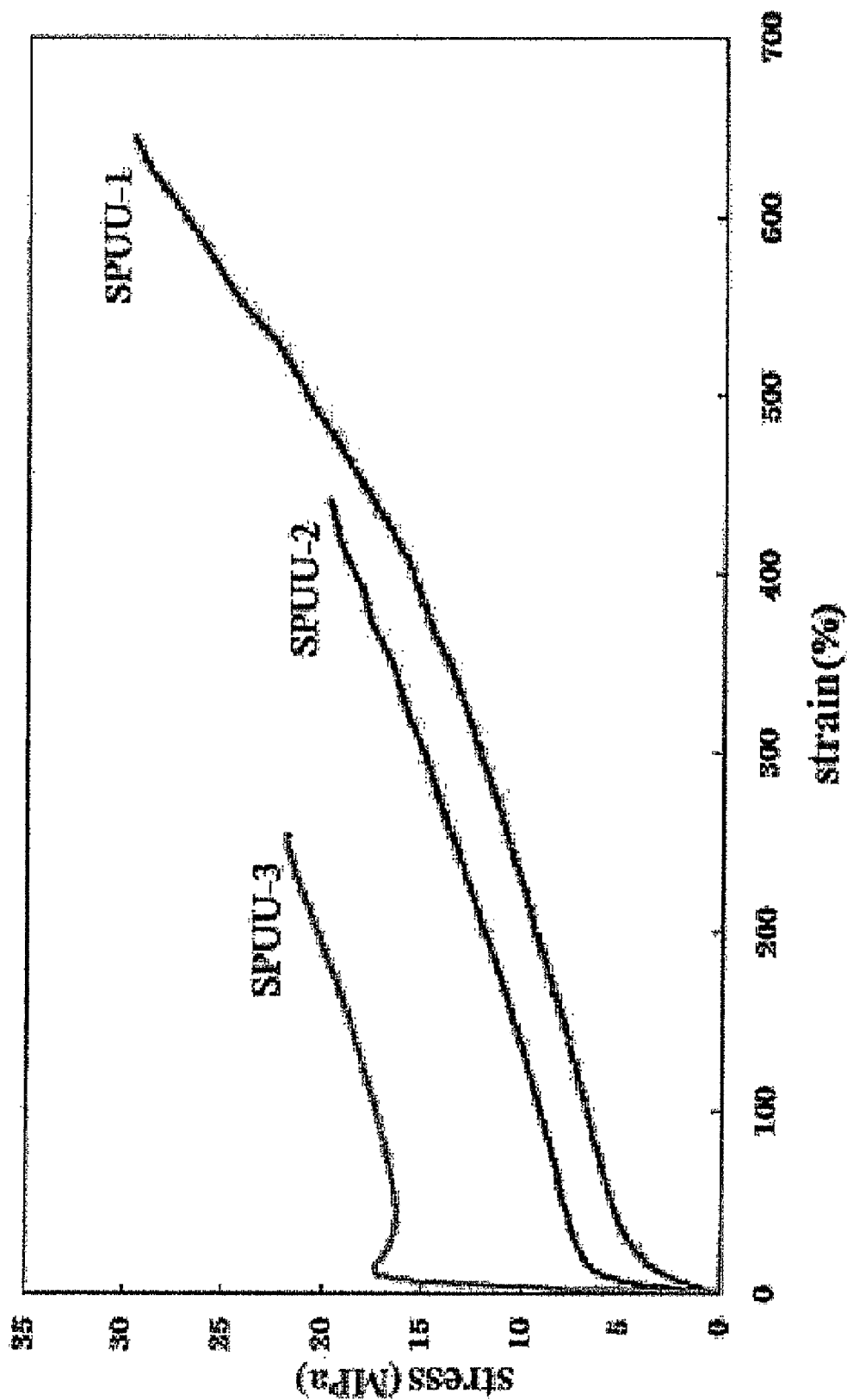

DIAMINE COMPOUND HAVING PHOSPHORYLCHOLINE GROUP, POLYMER THEREOF, AND PROCESS FOR PRODUCING THE POLYMER

FIELD OF THE INVENTION

The present invention relates to diamine compounds having a phosphorylcholine group, polymers with a phosphorylcholine side chain that are obtained by polymerizing the compound as a monomer, and processes for producing the polymers. The polymers of the invention have high antithrombotic activity and are useful as biocompatible materials permitting only small adsorption of biogenic substances such as proteins thereto.

BACKGROUND OF THE INVENTION

It is known that living organisms react defensively against implanted artificial organs or medical devices to show prominent rejections such as blood coagulation, inflammation and encapsulation. This is a result of a series of bioactivation reactions that start from adsorption of proteins on materials constituting the artificial organs and medical devices. Accordingly, treatments with artificial organs or medical devices entail simultaneous use of drugs, for example anticoagulants such as heparin and immunosuppressants.

However, side effects of these drugs are more serious when the treatment extends over a long period of time or as patients advance in age.

To solve these problems, a series of medical materials known as biocompatible materials have been developed. Of such biocompatible materials, polymers having phosphorylcholine groups that are phospholipid polar groups have been developed focusing on the structure of biomembrane surfaces. In detail, polymers that have structural units from 2-methacryloyloxyethyl phosphorylcholine (MPC) (hereinafter "MPC polymers") show particularly high biocompatibility (Non-Patent Document 1).

MPC is a methacrylate and homopolymers thereof are water soluble, whilst copolymers thereof with vinyl monomers are water-insoluble MPC polymers having a structure suitable for covering the surface of medical devices. By coating the device surface with the water-insoluble MPC polymers, blood coagulation can be prevented without anticoagulants, and subcutaneous implantation tests have proven very high biocompatibility (Non-Patent Document 2). The water-insoluble MPC polymers have been used as surface-coating materials for medical devices that are clinically applied in the United States and Europe. An increasing number of such coated devices have been approved also in Japan. The polymers are thus expected to dramatically improve the effectiveness of medical devices and to improve patient's quality of life.

However, mechanical strength, water resistance and autoclave sterilization heat resistance are still insufficient because of the MPC's inherent hydrophilicity and the flexible main chain structures of the MPC/vinyl copolymers. There is therefore a need for materials that exhibit improved mechanical strength, water resistance and heat resistance while maintaining the superior biocompatibility and processability of the MPC polymers.

The present inventors have reported specific diamine compounds having a phosphorylcholine group, and polymers from the compound as a monomer that have excellent water resistance, heat resistance and biocompatibility (Patent Document 1).

Non-Patent Document 1: Ishihara et al., Polymer Journal, Vol. 22, p. 355, 1990

Non-Patent Document 2: Ishihara et al., Geka (Surgery), Vol. 61, p. 132, 1999

Patent Document 1: WO 2004/074298

The diamine compounds, however, show relatively low reactivity in polymerization. Accordingly, there should be developed novel diamine compounds with a phosphorylcholine group that have higher polymerization reactivity (hereinafter, the highly polymerizable phosphorylcholine group-containing diamine compounds). With such highly polymerizable phosphorylcholine group-containing diamine compounds, it is expected that high-molecular weight polymers may be easily obtained and mechanical strength, water resistance, heat resistance and biocompatibility of the polymers may be improved, thereby increasing utility as materials.

It is therefore an object of the invention to provide highly polymerizable phosphorylcholine group-containing diamine compounds, high-molecular weight polymers from the highly polymerizable phosphorylcholine group-containing diamine compound as a monomer that achieve improved mechanical strength, water resistance and heat resistance while maintaining the excellent biocompatibility and processability of the MPC polymers, and processes for producing the polymers.

The present inventors diligently studied to achieve the above object in view of the aforesaid circumstances. They have then found that diamine compounds having a specific structure can give polymers capable of improved mechanical strength, water resistance, heat resistance and biocompatibility. The present invention has been completed based on the finding.

SUMMARY OF THE INVENTION

The present invention relates to the following.

A diamine compound having a phosphorylcholine group according to the present invention is represented by Formula (I):

[Chem. 1]

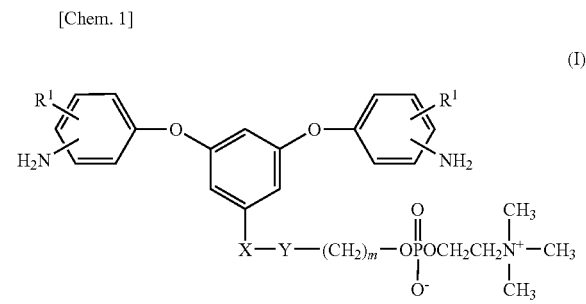

wherein two $R^1$ may be the same or different from each other and are each a hydrogen atom or an alkyl group having 1 to 6 carbon atoms; X is a single bond, an oxygen atom, —COO—, —OOC—, —CONH—, —NH—, —NHCO—, —NR²— or —CH₂O—; Y is a single bond, an alkylene group having 1 to 6 carbon atoms or an oligooxyalkylene group; $R^2$ is an alkyl group having 1 to 6 carbon atoms; and m is an integer of 1 to 6.

A polymer according to the present invention comprises at least 1 mol % of a structural unit with a phosphorylcholine side chain represented by Formula (II) below and has a number average molecular weight of not less than 5,000:

[Chem. 2]

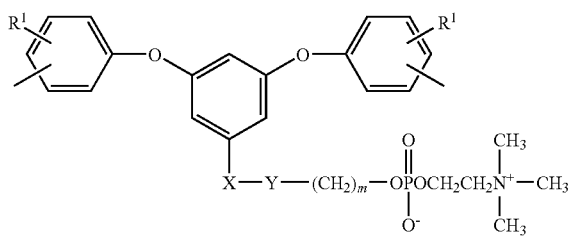

(II)

wherein two $R^1$ may be the same or different from each other and are each a hydrogen atom or an alkyl group having 1 to 6 carbon atoms; X is a single bond, an oxygen atom, —COO—, —OOC—, —CONH—, —NH—, —NHCO—, —$NR^2$— or —$CH_2O$—; Y is a single bond, an alkylene group having 1 to 6 carbon atoms or an oligooxyalkylene group; $R^2$ is an alkyl group having 1 to 6 carbon atoms; and m is an integer of 1 to 6.

The polymer preferably has an amide bond, a urethane bond, a urea bond or an imide bond in its main chain skeleton.

A process for producing polymers according to the present invention comprises polycondensation or polyaddition of reacting a diamine compound having a phosphorylcholine group of Formula (I) below with another polymerizable monomer, or comprises reacting the diamine compound having a phosphorylcholine group with a functional group-terminated prepolymer capable of reacting with the diamine compound:

[Chem. 3]

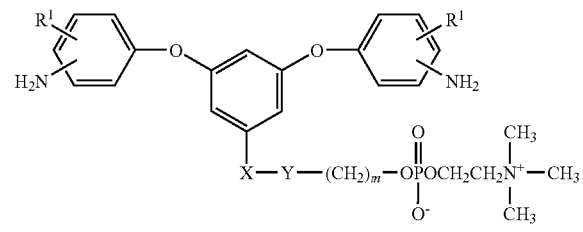

(I)

wherein two $R^1$ may be the same or different from each other and are each a hydrogen atom or an alkyl group having 1 to 6 carbon atoms; X is a single bond, an oxygen atom, —COO—, —OOC—, —CONH—, —NH—, —NHCO—, —$NR^2$— or —$CH_2O$—; Y is a single bond, an alkylene group having 1 to 6 carbon atoms or an oligooxyalkylene group; $R^2$ is an alkyl group having 1 to 6 carbon atoms; and m is an integer of 1 to 6.

The other polymerizable monomer is preferably one or more monomers selected from dicarboxylic acids, dicarboxylic acid derivatives, tetracarboxylic dianhydrides and diisocyanate compounds.

The functional group-terminated prepolymer is preferably an isocyanate group-terminated urethane prepolymer obtained by reacting a diisocyanate compound and a diol compound.

In the process of the invention, a diamine compound having no phosphorylcholine group is preferably co-present in the polycondensation or polyaddition reaction of the diamine compound having a phosphorylcholine group with another polymerizable monomer, or in the reaction of the diamine compound having a phosphorylcholine group with the functional group-terminated prepolymer.

ADVANTAGES OF THE INVENTION

The diamine compounds of the invention show high polymerization reactivity and can easily give high-molecular weight polymers having a phosphorylcholine side chain. The obtained polymers of the invention have excellent mechanical strength, water resistance, heat resistance and biocompatibility as well as good forming processability. Accordingly, the polymers may be used for the manufacturing of artificial organs such as artificial blood vessels and other various medical devices that have excellent mechanical strength, water resistance, heat resistance and biocompatibility.

BRIEF DESCRIPTION OF THE DRAWING

The drawing shows stress-strain curves of segmented polyurethane-urea films.

PREFERRED EMBODIMENTS OF THE INVENTION

The present invention will be described in detail hereinbelow.
<Diamine Compounds>
The diamine compounds of the invention have a phosphorylcholine functional group and are represented by Formula (I):

[Chem. 4]

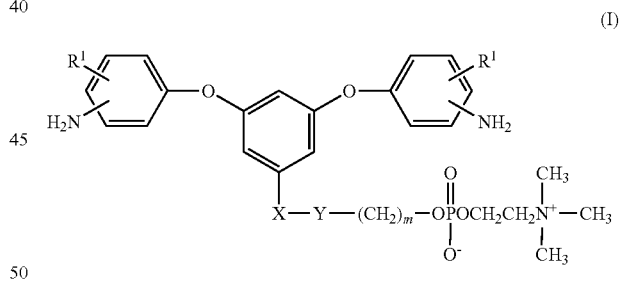

(I)

wherein two $R^1$ may be the same or different from each other and are each a hydrogen atom or a C1-6 alkyl group; X is a single bond, an oxygen atom, —COO—, —OOC—, —CONH—, —NH—, —NHCO—, —$NR^2$— or —$CH_2O$—; Y is a single bond, a C1-6 alkylene group or an oligooxyalkylene group; $R^2$ is a C1-6 alkyl group; and m is an integer of 1 to 6.

Examples of the alkyl groups having 1 to 6 carbon atoms indicated by $R^1$ in Formula (I) include methyl, ethyl, propyl, isopropyl, butyl, sec-butyl, tert-butyl, pentyl and hexyl groups.

Examples of the alkylene groups having 1 to 6 carbon atoms indicated by Y in Formula (I) include —$(CH_2)_x$— (where x is an integer of 1 to 6). Examples of the oligooxyalkylene groups include oxyalkylene groups of 2 to 12 carbon atoms and 1 to 3 oxygen atoms, such as —$(CH_2CH_2O)_y$—, —(CH$_2$CH$_2$CH$_2$O)$_y$— and —(CH$_2$CH$_2$CH$_2$CH$_2$O)$_y$— (where y is an integer of 1 to 3).

When X in Formula (I) represents —NR$^2$—, the alkyl groups having 1 to 6 carbon atoms indicated by R$^2$ include methyl, ethyl, propyl, isopropyl, butyl, sec-butyl, tert-butyl, pentyl and hexyl groups.

Of the diamine compounds of Formula (I), preferred examples are compounds wherein two R$^1$ in Formula (I) are both hydrogen atoms, as represented by Formula (Ia) below:

[Chem. 5]

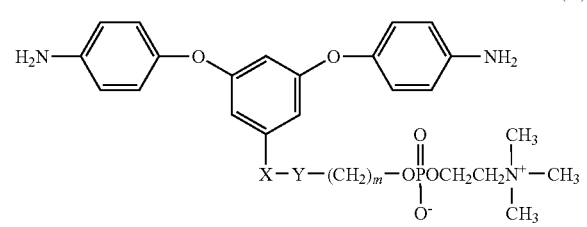

(Ia)

wherein X, Y and m are as defined in Formula (I).

<Production of Diamine Compounds>

The diamine compounds with a phosphorylcholine group represented by Formula (I) may be produced for example by the following method.

A dinitro compound with a hydroxyl group represented by Formula (III):

[Chem. 6]

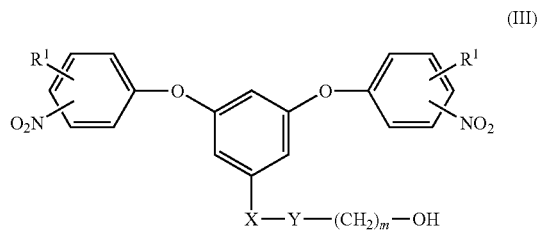

(III)

is reacted with 2-chloro-2-oxo-1,3,2-dioxaphosphorane (hereinafter COP) to synthesize a dinitro compound with a phosphoryl group represented by Formula (IV):

[Chem. 7]

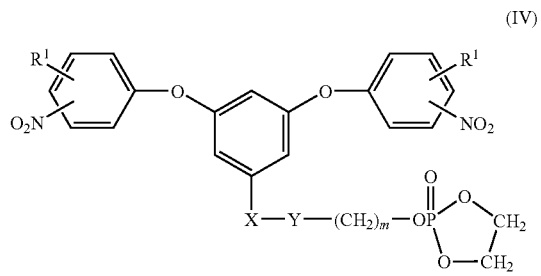

(IV)

Subsequently, the dinitro compound (IV) is reacted with trimethylamine to afford a dinitro compound with a phosphorylcholine group represented by Formula (V):

[Chem. 8]

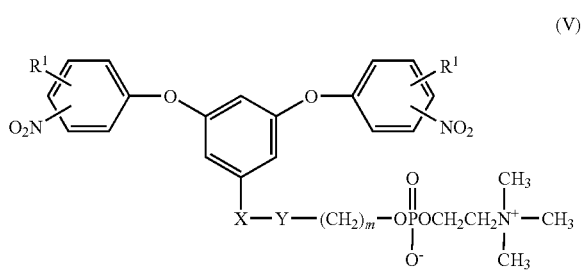

(V)

Thereafter, the nitro groups in the compound (V) are reduced to produce a diamine compound with a phosphorylcholine group represented by Formula (I).

In Formulae (III) to (V) above, R$^1$, X, Y and m are as defined in Formula (I).

The dinitro compound with a hydroxyl group represented by Formula (III) may be easily synthesized from commercially available compounds by known reaction methods, for example as described in Example 1 later.

In the reaction between the dinitro compound of Formula (III) (dinitro compound (III)) and COP, these compounds are preferably used in a molar ratio (dinitro compound (III):COP) of 1:1 to 1:5 and in the presence of a tertiary amine such as triethylamine to capture hydrogen chloride generated or while blowing an inert gas into the reaction zone to expel the hydrogen chloride.

In the subsequent ring-opening addition reaction between the dinitro compound of Formula (IV) (dinitro compound (IV)) and trimethylamine (hereinafter TMA), they are preferably used in a molar ratio (dinitro compound (IV):TMA) of 1:1 to 1:5.

The reduction of the nitro groups in the dinitro compound of Formula (V) (dinitro compound (V)) may be easily conducted by reaction of the dinitro compound (V) with a typical reducing agent such as diborane, lithium borohydride, sodium borohydride, sodium aluminum hydride, sodium dialkoxyaluminum hydride or sodium diethylaluminum hydride. The reaction may proceed more favorably in the presence of a catalyst such as tin chloride. It is also possible to carry out catalytic reduction reaction in a hydrogen atmosphere under catalysis by a metal such as nickel, platinum, palladium or rhodium.

The above reactions are preferably carried out at atmospheric pressure or under pressure in an appropriate solvent. The solvents used herein may be any inert solvents such as methanol, ethanol, tetrahydrofuran, dimethoxyethane, dioxane, benzene and toluene. The reaction temperature is in the range of −100 to 150° C., and preferably −50 to 100° C.

<Polymers and Production Processes>

<Polymers Having Phosphorylcholine Side Chain>

The polymers according to the present invention contain at least 1 mol % of a structural unit with a phosphorylcholine group and has a number average molecular weight of not less than 5,000. The structural unit is represented by Formula (II):

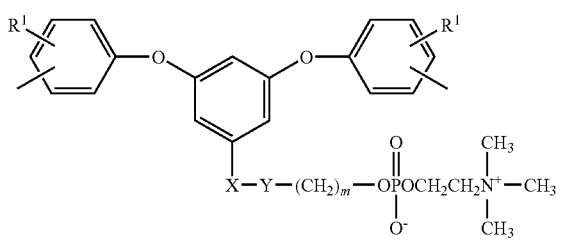

wherein $R^1$, X, Y and m are as defined in Formula (I).

The number average molecular weight of the polymers is generally not less than 5,000, preferably not less than 10,000 and more preferably from 10,000 to 500,000. The number average molecular weight in this range ensures good mechanical strength, processability, heat resistance and stability. The number average molecular weight is measured by gel permeation chromatography (GPC) relative to polystyrene standards.

In order for the polymer to exhibit biocompatibility, the polymer should contain at least 1 mol % of the structural unit with a phosphorylcholine group represented by Formula (II). Where higher biocompatibility is required depending on the intended use, the structural units are desirably contained at 5 mol % or above, and more preferably at 10 mol % or above.

The content of the structural units with a phosphorylcholine group represented by Formula (II) in the polymer may be easily controlled by adjusting the feeding ratio of the diamine compound with a phosphorylcholine group of Formula (I) (on a molar basis relative to other materials) in the polymerization reaction described later.

Preferred structural units represented by Formula (II) include structural units wherein two $R^1$ in Formula (II) are both hydrogen atoms, as represented by Formula (IIa) below:

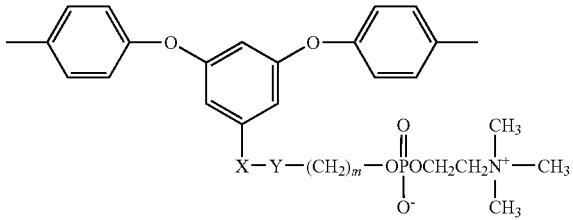

wherein X, Y and m are as defined in Formula (I).

The polymers including the structural units of Formula (II) preferably have an amide bond, a urethane bond, a urea bond or an imide bond in the main chain skeleton.

<Polymer Production Processes>

The polymers of the present invention may be produced by polycondensation or polyaddition of reacting the diamine compound having a phosphorylcholine group of Formula (I) with another polymerizable monomer, or by reacting the diamine compound having a phosphorylcholine group with a functional group-terminated prepolymer capable of reacting with the diamine compound. Herein, the words "other polymerizable monomers" refer to monomers other than and polymerizable with the diamine compounds with a phosphorylcholine group represented by Formula (I).

When the diamine compound of Formula (I) is subjected to the polycondensation or polyaddition reaction with a dicarboxylic acid or a dicarboxylic acid derivative as another polymerizable monomer, a polyamide having an amide bond in its main chain skeleton may be obtained. Alternatively, the reaction with a tetracarboxylic dianhydride to form a polyamide acid followed by imidation by chemical or heat treatment affords a polyimide having an imide bond in its main chain skeleton. The use of a diisocyanate compound gives a polyurea having a urea bond in its main chain skeleton.

It is preferable that the polycondensation or polyaddition reaction is carried out in the presence of known diamine compounds (hereinafter, other diamine compounds) other than the diamine compounds of the invention, and preferably in the presence of diamine compounds having no phosphorylcholine group. The use of such other diamine compounds leads to improved mechanical strength, water resistance and heat resistance of the obtainable polymers. Specific examples of such known diamine compounds include 1,4-phenylenediamine, 1,3-phenylenediamine, 2,5-diaminotoluene, 2,6-diaminotoluene, 4,4'-diaminobiphenyl, 3,3'-dimethyl-4,4'-diaminobiphenyl, 3,3'-dimethoxy-4,4'-diaminobiphenyl, 4,4'-diaminodiphenylmethane, 4,4'-diamino-3,3'-dimethyldiphenylmethane, 4,4'-diaminodiphenyl ether, 2,2-bis(4-aminophenyl)propane, 4,4'-diaminodiphenylsulfone, 4,4'-diaminobenzophenone, 1,4-bis(4-aminophenyl)benzene, 1,4-bis(4-aminophenoxy)benzene, 4,4'-bis(4-aminophenoxy)diphenylsulfone, 2,2-bis[4-(4-aminophenoxy)phenyl]propane, bis(4-aminocyclohexyl)methane, piperazine, 2-methylpiperazine, ethylenediamine, 1,3-diaminopropane, tetramethylenediamine, pentamethylenediamine, hexamethylenediamine, heptamethylenediamine, octamethylenediamine, nonamethylenediamine, decamethylenediamine and dodecamethylenediamine. These may be used singly, or two or more kinds may be used in combination. When the other diamine compounds are used, the diamine compound according to the invention is mixed therewith such that the diamine compound of the invention accounts for not less than 1 mol %, preferably not less than 5 mol %, and more preferably from 5 to 50 mol % relative to all the diamine compounds. This proportion ensures that the obtainable polymer will show biocompatibility.

The dicarboxylic acids and dicarboxylic acid derivatives usable as the other polymerizable monomers include compounds represented by Formula (VI):

wherein $Y^1$ is a divalent organic group, and preferably a divalent organic residue derived from dicarboxylic acid; and $X^1$ independently at each occurrence is a hydroxyl group, a halogen atom or an alkoxy group. Accordingly, the recurring units of the polyamides obtained in this case, that is, the recurring units containing the structural units of Formula (II)

of the polymers according to the invention are represented by Formula (VII):

[Chem. 12]

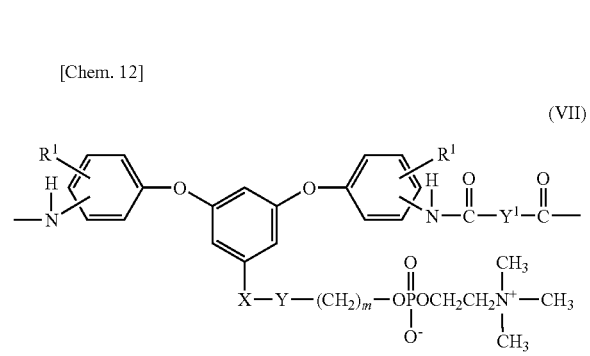

(VII)

wherein $Y^1$ is a divalent organic group, and preferably a divalent organic residue derived from dicarboxylic acid; and $R^1$, X, Y and m are as defined in Formula (II).

Specific examples of the dicarboxylic acids and derivatives thereof represented by Formula (VI) include phthalic acid, terephthalic acid, isophthalic acid, 2,6-naphthalenedicarboxylic acid, 1,6-naphthalenedicarboxylic acid, 2,6-anthracenedicarboxylic acid, 1,6-anthracenedicarboxylic acid, 4,4'-biphenyldicarboxylic acid, 4,4'-diphenylmethanedicarboxylic acid, 4,4'-diphenyl ether dicarboxylic acid, 2,2-bis(4-carboxyphenyl)propane, 2,2-bis[4-(4-carboxyphenylphenoxy)phenyl]propane, oxalic acid, succinic acid, fumaric acid, maleic acid, malonic acid, succinic acid, glutaric acid, adipic acid, pimelic acid, suberic acid, azelaic acid, sebacic acid, 1,9-nonanedicarboxylic acid, 1,10-decanedicarboxylic acid, and halides and alkyl esters of these dicarboxylic acids. They may be used singly, or two or more kinds may be used in combination.

The tetracarboxylic dianhydrides usable as the other polymerizable monomers include compounds represented by Formula (VIII):

[Chem. 13]

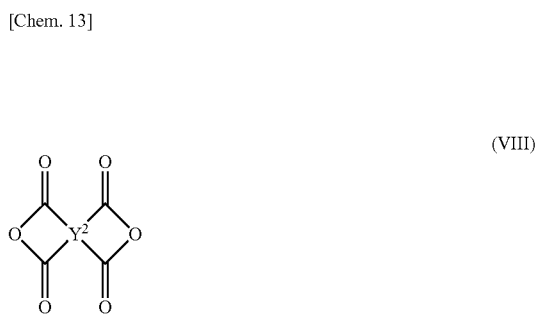

(VIII)

wherein $Y^2$ is a tetravalent organic group, and preferably a tetravalent organic residue derived from tetracarboxylic acid. Accordingly, a polyimide is obtained in this case via a polyamide acid and by known chemical or heat treatment of the polyamide acid. The recurring units of the polyimides in this case, that is, the recurring units containing the structural units of Formula (II) of the polymers according to the invention are represented by Formula (IX):

[Chem. 14]

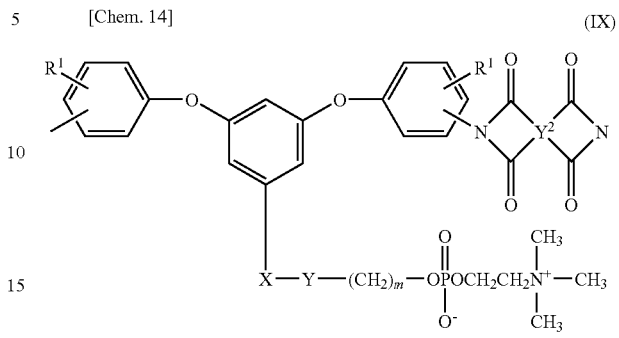

(IX)

wherein $Y^2$ is a tetravalent organic group, and preferably a tetravalent organic residue derived from tetracarboxylic acid; and $R^1$, X, Y and m are as defined in Formula (II).

Specific examples of the tetracarboxylic dianhydrides represented by Formula (VIII) include pyromellitic dianhydride, 2,3,6,7-naphthalenetetracarboxylic dianhydride, 1,2,5,6-naphthalenetetracarboxylic dianhydride, 1,4,5,8-naphthalenetetracarboxylic dianhydride, 2,3,6,7-anthracenetetracarboxylic dianhydride, 1,2,5,6-anthracenetetracarboxylic dianhydride, 3,3',4,4'-diphenyltetracarboxylic dianhydride, bis(3,4-dicarboxyphenyl)ether dianhydride, 3,3',4,4'-benzophenonetetracarboxylic dianhydride, bis(3,4-dicarboxyphenyl)sulfone dianhydride, bis(3,4-dicarboxyphenyl) methane dianhydride, 2,2-bis(3,4-dicarboxyphenyl)propane dianhydride, 1,1,1,3,3,3-hexafluoro-2,2-bis(3,4-dicarboxyphenyl)propane dianhydride, bis(3,4-dicarboxyphenyl) dimethylsilane dianhydride, bis(3,4-dicarboxyphenyl)diphenylsilane dianhydride, 2,3,5,6-pyridinetetracarboxylic dianhydride, 2,6-bis(3,4-dicarboxyphenoxy)pyridine dianhydride, cyclobutanetetracarboxylic dianhydride, cyclopentanetetracarboxylic dianhydride, cyclohexanetetracarboxylic dianhydride and 3,4-dicarboxy-1,2,3,4-tetrahydro-1-naphthalenesuccinic tetracarboxylic dianhydride. They may be used singly, or two or more kinds may be used in combination.

The diisocyanate compounds employable as the other polymerizable monomers include compounds represented by Formula (X):

[Chem. 15]

$$O=C=N-Y^3-N=C=O \qquad (X)$$

wherein $Y^3$ is a divalent organic group, and preferably a divalent organic residue derived from diisocyanate compound. Accordingly, the recurring units of the polyureas obtained in this case, that is, the recurring units containing the structural units of Formula (II) of the polymers according to the invention are represented by Formula (XI):

[Chem. 16]

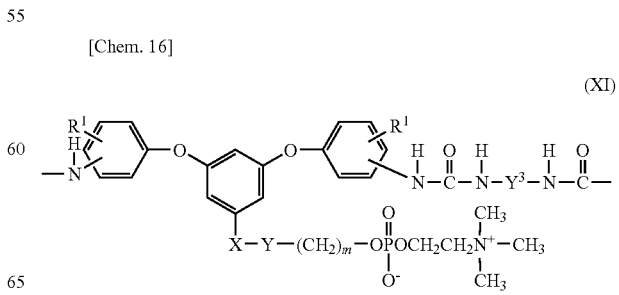

(XI)

wherein $Y^3$ is a divalent organic group, and preferably a divalent diisocyanate compound residue; and $R^1$, X, Y and m are as defined in Formula (II).

Specific examples of the diisocyanate compounds represented by Formula (X) include 1,4-phenylene diisocyanate, 1,3-phenylene diisocyanate, 1,4-xylylene diisocyanate, 1,3-xylylene diisocyanate, 2,4-toluoylene diisocyanate, 2,5-toluoylene diisocyanate, 4,4'-biphenylene diisocyanate, 4,4'-diphenyl ether diisocyanate, 4,4'-diphenylmethane diisocyanate, 4,4'-(2,2-diphenylpropane) diisocyanate, tetramethylene diisocyanate, pentamethylene diisocyanate, hexamethylene diisocyanate, heptamethylene diisocyanate and octamethylene diisocyanate. They may be used singly, or two or more kinds may be used in combination.

The polycondensation or polyaddition reaction of the diamine compounds having a phosphorylcholine group of Formula (I) and the other polymerizable monomers may be performed according to known literature methods (e.g., "Macromolecular Synthesis" edited by J. A. Moore, John Wiley & Sons, New York, 1997, "Polymer Syntheses" edited by S. R. Sandler and W. Karo, Academic. Press, Inc., Boston, 1992, and "Shin Koubunshi Jikkengaku (New Polymer Experiments)" edited by The Society of Polymer Science, Japan, Vol. 3, "Koubunshi no Gousei Hannou (Polymer Synthesis Reactions) (2)—Shukugoukei Koubunshi no Gousei (Syntheses of Condensation Polymers)", Kyoritsu Shuppan Co., Ltd., 1996).

In an embodiment of the invention, the diamine compound with a phosphorylcholine group represented by Formula (I) may be reacted with a functional group-terminated prepolymer capable of reacting with the diamine compound, whereby mechanical strength, water resistance and heat resistance of the polymer may be enhanced. Herein, the words "functional group-terminated prepolymers" refer to prepolymers that have a functional group at either or both of a main chain terminal and a side chain terminal and wherein the functional group is capable of reacting with the diamine compound, in particular with the amino groups of the diamine compound.

Preferred examples of the functional group-terminated prepolymers include isocyanate group-terminated urethane prepolymers obtained by reacting an excess of a diisocyanate compound with a diol compound. In detail, an excess of a diisocyanate compound is polymerized with a diol compound to afford an isocyanate group-terminated urethane prepolymer, and the prepolymer is reacted with the diamine compound of the present invention to give a poly(urethane-urea) having a urethane bond and a urea bond in its main chain skeleton.

Specific examples of the diol compounds used herein include hydroquinone, 1,3-phenylene dial, 1,4-xylylene diol, 1,3-xylylene diol, 2,4-toluoylene diol, 2,5-toluoylene diol, 4,4'-biphenylene diol, 4,4'-diphenyl ether diol, 4,4'-diphenylmethane diol, bisphenol A, ethylene glycol, propylene glycol, tetramethylene glycol, pentamethylene glycol, hexamethylene glycol, heptamethylene glycol, octamethylene glycol, polyethylene glycol, polypropylene glycol, polytetraethylene oxide, α,ω-bis(hydroxypropyl)polydimethylsiloxane and α,ω-bis(hydroxyethoxypropyl)polydimethylsiloxane. These may be used singly, or two or more kinds may be used in combination.

Similar to the aforementioned embodiment, it is preferable in this preferred embodiment to use the other diamine compounds, preferably diamine compounds having no phosphorylcholine group, in the reaction between the diamine compound of the present invention and the functional group-terminated prepolymer, whereby the mechanical strength, water resistance and heat resistance of the polymer may be improved. When the other diamine compounds are used, the diamine compound according to the invention is mixed therewith such that the diamine compound of the invention accounts for not less than 1 mol %, preferably not less than 5 mol %, and more preferably from 5 to 50 mol % relative to all the diamine compounds. This proportion ensures that the obtainable polymer will show biocompatibility.

EXAMPLES

The present invention will be described in greater detail by Examples and Comparative Examples hereinafter, but it should be construed that the invention is in no way limited to those Examples.

In Examples and Comparative Examples, the molecular weight was measured by GPC (gel permeation chromatography) under the following conditions:
<GPC Conditions>
Liquid pump: CCPD (manufactured by TOSOH CORPORATION)
Column oven: CO-8010 (manufactured by TOSOH CORPORATION)
Separation columns: five TSK gel Multipore $H_{XL}$-M connected in series
Detector: RI-8010 (differential refractometer) (manufactured by TOSOH CORPORATION)
Column temperature: 45° C.
Mobile phase: dimethylformamide
Mobile speed: 1.0 ml/min
Sample concentration: 0.5 wt %
Sample injection amount: 100 μl
Standards: monodisperse polystyrene standards Example 1

Synthesis 1 of Diamine Compound According to the Invention

[Chem. 17]

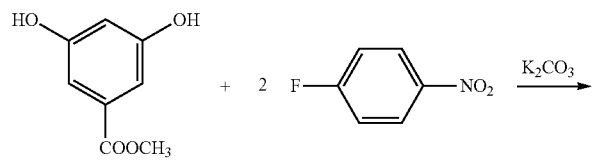

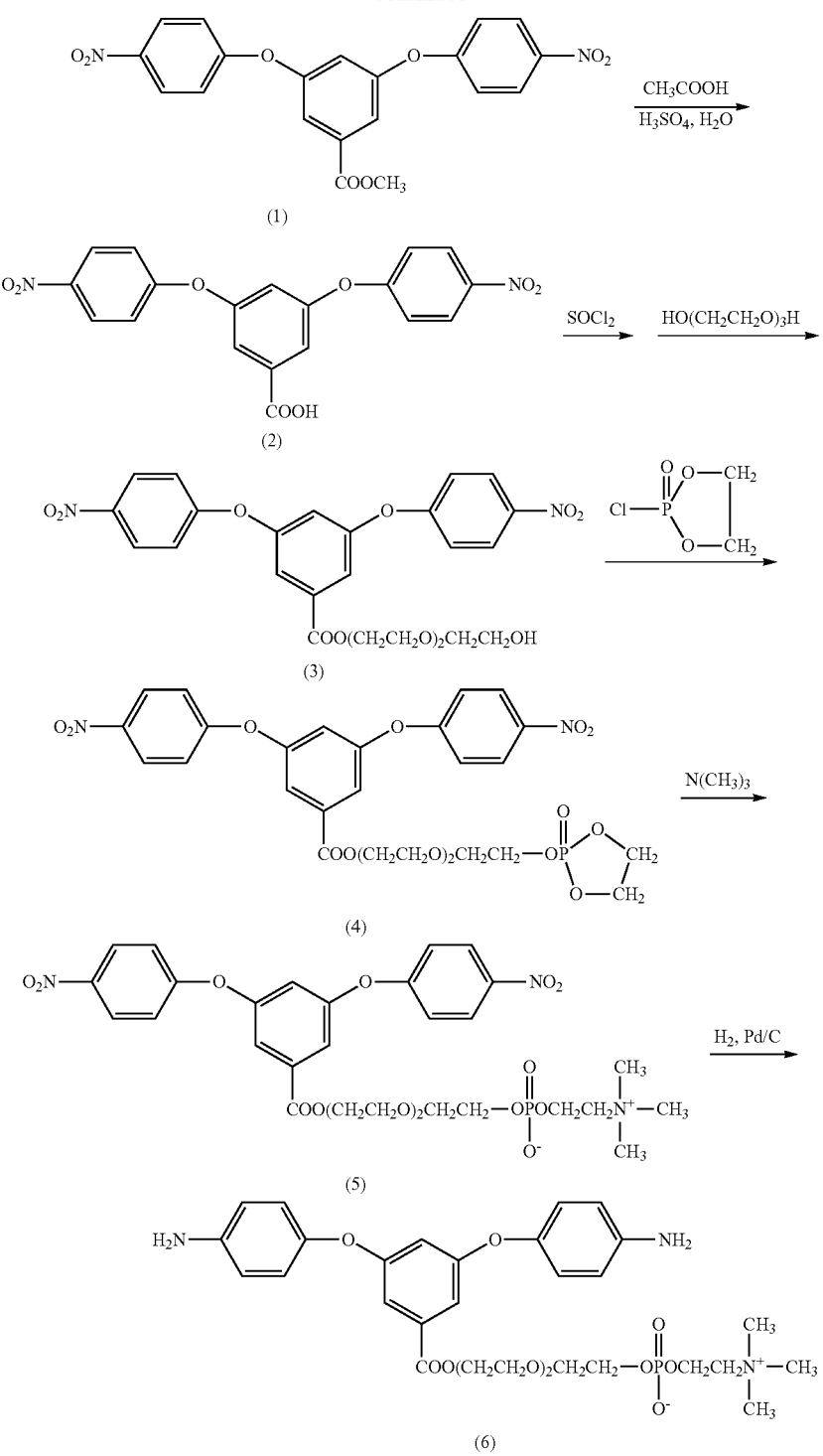

<Synthesis of Compound (1)>

In an evaporation flask, methyl 3,5-dihydroxybenzoate (5.00 g, 29.7 mmol) was dissolved in dimethylacetamide (50 ml). 4-Fluoronitrobenzene (8.39 g, 59.5 mmol) and potassium carbonate (8.22 g, 59.5 mmol) were added to the solution, and reaction was carried out at 85° C. for 5 hours. After the completion of the reaction, the solution was poured into an excess of distilled water, and the resultant precipitate was suction filtered and was heat vacuum dried to give a compound (1) as a white solid (weight: 10.4 g, yield: 85.4%). The structure of the compound was determined from the $^1$H-NMR and IR spectra given below:

$^1$H-NMR, δ (400 MHz, DMSO-$d_6$, ppm): 8.28 (4H, m), 7.53 (2H, s), 7.32 (1H, s), 7.27 (4H, m), 3.85 (3H, s).

IR, ν (KBr, cm$^{-1}$): 3120, 3082, 1709 (C=O), 1604, 1582, 1520, 1508, 1489 (—NO$_2$), 1441, 1352 (—NO$_2$), 1308, 1232, 1220 (C—O—C), 1167, 1126, 1105, 1005, 993, 851, 773, 750.

<Synthesis of Compound (2)>

In an evaporation flask, the compound (1) from the above reaction (10.4 g, 25.4 mmol), acetic acid (75 ml), sulfuric acid (30 ml) and distilled water (20 ml) were mixed together and reacted at 120° C. for 6 hours. After the completion of the reaction, the solution was poured into an excess of distilled water, and the resultant precipitate was suction filtered and was heat vacuum dried to give a compound (2) as a white solid (weight: 9.28 g, yield: 92.3%). The structure of the compound was determined from the $^1$H-NMR and IR spectra given below:

$^1$H-NMR, δ (400 MHz, DMSO-d$_6$, ppm): 12.2 (1H, bs), 8.28 (4H, m), 7.51 (2H, s), 7.29 (1H, s), 7.26 (4H, m).

IR, ν (KBr, cm$^{-1}$): 3110, 3080, 2960 (COOH), 2845, 1693 (C=O), 1578, 1514, 1487 (—NO$_2$), 1423, 1340 (—NO$_2$), 1305, 1221 (C—O—C), 1170, 1111, 995, 947, 891, 858, 754.

<Synthesis of Compound (3)>

Under a stream of argon, the compound (2) obtained by reaction as described above (12.9 g, 32.6 mmol), thionylchloride (100 ml) and dimethylformamide (0.2 ml) were mixed and reacted together in a three-necked flask under reflux for 6 hours. The solvent was evaporated, and a white solid resulted. In an argon atmosphere, a solution of the white solid in dry tetrahydrofuran (110 ml) was slowly added dropwise to a three-necked flask which contained a solution of triethylene glycol (43.3 ml, 326 mmol), dry tetrahydrofuran (250 ml) and dry triethylamine (9.05 ml, 65.2 mmol), with the flask in an ice water bath. After the completion of the dropwise addition, the mixture was stirred at room temperature overnight. Subsequently, the reaction solution was extracted with chloroform and the extract was washed with distilled water. The organic phase was dehydrated with sodium sulfate and then filtered, and the solvent was distilled away under reduced pressure. Thereafter, the distillate was purified by silica gel column chromatography (developing solvents: hexane/ethyl acetate=1/2 (by volume)) to give an alcohol compound represented by Formula (3) above as a yellow liquid (weight: 15.1 g, yield: 87.9%). The structure of the compound was determined from the $^1$H-NMR and IR spectra given below:

$^1$H-NMR, δ (400 MHz, DMSO-d$_6$, ppm): 8.28 (4H, m), 7.55 (2H, s), 7.32 (1H, s), 7.28 (4H, m), 4.55 (1H, s), 4.40 (2H, s), 3.75 (2H, t, J=4.64 Hz), 3.57 (2H, t, J=1.34 Hz), 3.52 (4H, m), 3.40 (2H, t, J=2.81 Hz).

IR, ν (KBr, cm$^{-1}$): 3377 (—OH), 3150, 3084, 2980, 2940, 1728 (C=O), 1580, 1514, 1489 (—NO$_2$), 1448, 1348 (—NO$_2$), 1300, 1230, 1215 (C—O—C), 1163, 1113, 1074, 1001, 968, 893, 851, 750.

<Synthesis of Compound (4)>

In an argon atmosphere, the compound (3) from the above reaction (14.5 g, 27.4 mmol), dry tetrahydrofuran (140 ml) and dry triethylamine (15.2 g, 110 mmol) were mixed together in a three-necked flask. While stirring was performed with the flask in an ice water bath, 2-chloro-2-oxo-1,3,2-dioxaphosphorane (5.04 ml, 54.9 mmol) was slowly added dropwise. After the completion of the dropwise addition, the mixture was stirred at room temperature for 2 hours. Subsequently, the reaction solution was extracted with chloroform and the extract was washed with distilled water. The organic phase was dehydrated with sodium sulfate and then filtered, and the solvent was distilled away under reduced pressure. As a result, a phosphorane compound represented by Formula (4) above was obtained as a brown liquid (weight: 17.4 g, yield: 94.0%). The structure of the compound was determined from the $^1$H-NMR and IR spectra given below:

$^1$H-NMR, δ (400 MHz, DMSO-d$_6$, ppm): 8.28 (4H, m), 7.55 (2H, s), 7.32 (1H, s), 7.28 (4H, m), 4.40 (6H, m), 3.75 (2H, t, J=4.64 Hz), 3.58 (8H, m).

IR, ν (KBr, cm$^{-1}$): 3120, 3080, 2910, 2874, 1724 (C=O), 1580, 1518, 1489 (—NO$_2$), 1443, 1344 (—NO$_2$), 1300, 1235 (P=O), 1209 (C—O—C), 1111, 1032, 999, 968, 860, 750.

<Synthesis of Compound (5)>

In an argon atmosphere, the compound (4) from the above reaction (17.0 g, 26.9 mmol) was dissolved in dry acetonitrile (170 ml) in an evaporation flask. Trimethylamine (4.77 ml, 53.9 mmol) was added to the solution in an ice water bath, and the flask was tightly closed. Reaction was carried out at 60° C. overnight, and the solvent was distilled away under reduced pressure. As a result, a dinitro compound with a phosphorylcholine group represented by Formula (5) above was obtained as a white solid (weight: 18.6 g, yield: 93.3%). The structure of the compound was determined from the $^1$H-NMR and IR spectra given below:

$^1$H-NMR, δ (400 MHz, DMSO-d$_6$, ppm): 8.29 (4H, m), 7.55 (2H, s), 7.32 (1H, s), 7.29 (4H, m), 4.40 (2H, t, J=4.27 Hz), 4.09 (2H, t, J=6.59 Hz), 3.75 (4H, m), 3.56 (8H, m), 3.17 (9H, s).

IR, ν (KBr, cm$^{-1}$): 3120, 3080, 2940, 2895, 1722 (C=O), 1580, 1520, 1489 (—NO$_2$), 1445, 1382 (—NO$_2$), 1302, 1235 (P=O), 1209 (C—O—C), 1167, 1100, 1059, 999, 966, 860, 750.

<Synthesis of Compound (6)>

The compound (5) from the above reaction (34.8 g, 50.2 mmol) was dissolved in methanol (630 ml) in an evaporation flask. To the solution, 5% palladium-containing carbon powder (2.13 g, 1.00 mmol) was added, and the mixture was cooled to about −80° C. in an acetone-dry ice bath. The flask was purged with hydrogen, and reaction was carried out at room temperature overnight. The reaction solution was filtered through Celite. The filtrate was distilled under reduced pressure to approximately half the volume, and was poured into diethyl ether. The resultant precipitate was suction filtered and was dried under reduced pressure to afford a diamine compound with a phosphorylcholine group represented by Formula (6) above as a yellow solid (weight: 26.9 g, yield: 84.7%). The structure of the compound was determined from the $^1$H-NMR and IR spectra given below:

$^1$H-NMR, δ (400 MHz, DMSO-d$_6$, ppm): 6.97 (2H, s), 6.78 (4H, m), 6.67 (1H, s), 6.65 (4H, m), 4.30 (2H, t, J=4.27 Hz), 4.11 (4H, s), 3.77 (6H, m), 3.67 (8H, m), 3.16 (9H, s).

IR, ν (KBr, cm$^{-1}$): 3221 (—NH$_2$), 2955, 2883, 1720 (C=O), 1595, 1508, 1436, 1308, 1265 (P=O), 1209 (C—O—C), 1122, 1090, 1059, 1003, 959, 839, 768.

Example 2

Synthesis 1 of Polymer (Homopolymer) According to the Invention

[Chem. 18]

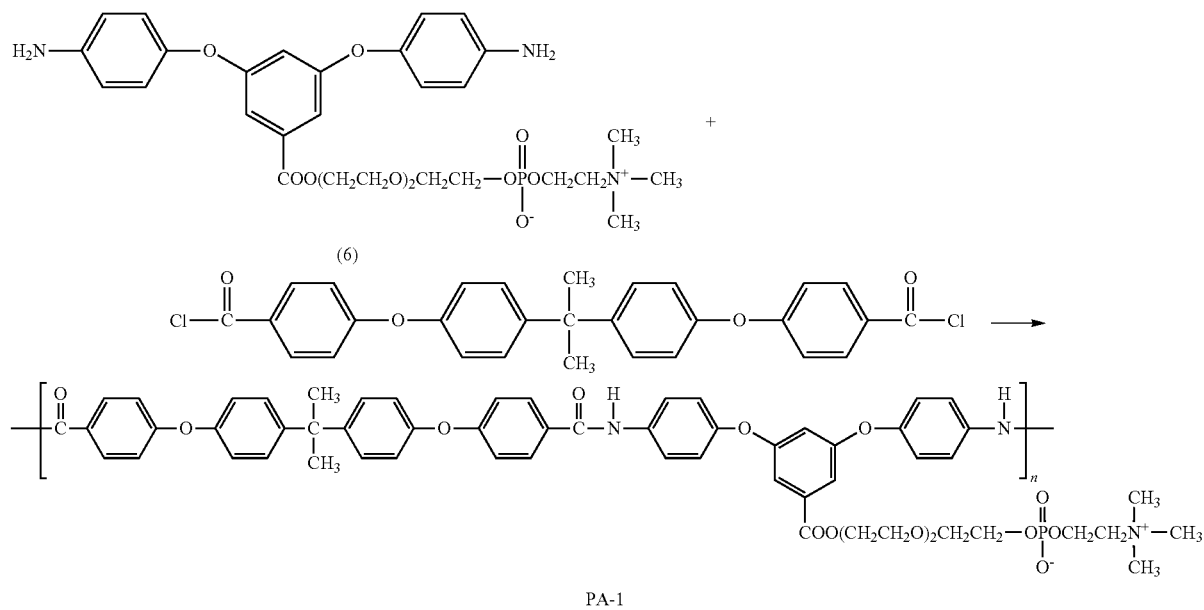

PA-1

In an argon atmosphere, the compound (6) from Example 1 (0.500 g, 0.789 mmol) and sodium hydrogencarbonate (0.133 g, 1.58 mmol) were dissolved in distilled water (2.63 ml) in a three-necked flask. A solution of 2,2-bis[(4-(4-chlorocarbonylphenoxy)phenyl]propane (0.400 g, 0.789 mmol) in chloroform (2.63 ml) was added dropwise to the solution over a period of 20 to 30 seconds to perform interfacial polycondensation. The resultant precipitate was sufficiently washed with methanol, suction filtered and dried under reduced pressure to give a polyamide with a phosphorylcholine group represented by Formula PA-1 above as a brown solid (weight: 0.619 g, yield: 73.4%). The structure of the polymer was determined from the IR spectrum given below:

IR, ν (KBr, cm$^{-1}$): 3422 (N—H), 2959, 1653 (C=O), 1499, 1437, 1406, 1242 (P=O), 1207 (C—O—C), 1169, 1115, 1010, 947, 840, 760.

The molecular weight of the polymer PA-1 was measured by GPC under the conditions described hereinabove, resulting in a number average molecular weight and a weight average molecular weight of $2.91 \times 10^5$ and $4.58 \times 10^5$, respectively, and the polymer PA-1 was found to be a high-molecular weight polymer. The polymer PA-1 did not have a glass transition temperature (softening point) in the range of 0 to 200° C. according to differential scanning calorimetry, and proved to be highly heat resistant.

The polymer PA-1 was found to be soluble in N-methylpyrrolidinone, partly soluble in dimethylformamide, and insoluble in water, methanol, ethanol, chloroform, acetone, tetrahydrofuran and acetonitrile. The PA-1's solubility in specific solvents provides advantageous forming processability in the material making such as coating and hollow filament production. Because of the insolubility in many other solvents, the materials may give super durable devices.

Separately, the polymer PA-1 was dissolved in N-methylpyrrolidinone and the solution was cast on a Teflon (registered trademark) substrate and was heated at 100° C. to evaporate the solvent. The resultant film was excellent in rigidity.

Example 3

Synthesis 2 of Polymer (Copolymer) According to the Invention

[Chem. 19]

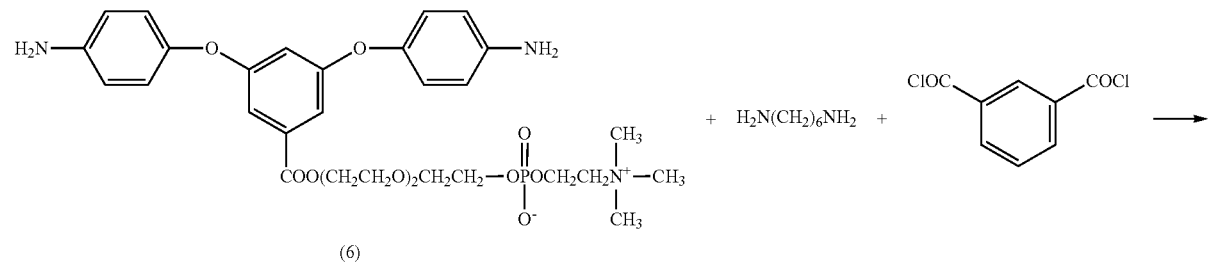

-continued

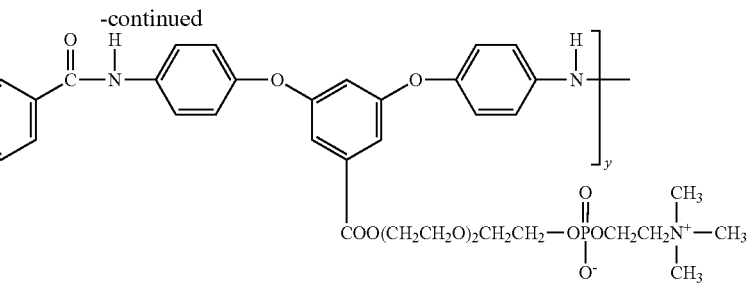

CPA-1, CPA-2, CPA-3

<Synthesis of CPA-1>

In an argon atmosphere, the compound (6) from Example 1 (0.167 g, 0.263 mmol), hexamethylenediamine (0.275 g, 2.37 mmol) and sodium hydrogencarbonate (0.442 g, 5.26 mmol) were dissolved in distilled water (8.77 ml) in a three-necked flask. A solution of isophthalic acid chloride (0.534 g, 2.63 mmol) in chloroform (8.77 ml) was added dropwise to the solution over a period of 20 to 30 seconds to perform interfacial polycondensation. The resultant precipitate was sufficiently washed with methanol, suction filtered and dried under reduced pressure to give a polyamide copolymer with a phosphorylcholine group represented by Formula CPA-1 above as a yellow solid (weight: 0.697 g, yield: 88.9%). The structure of the copolymer was determined from the IR spectrum given below. From the $^1$H-NMR spectrum, the copolymerization ratio (on a molar basis) of the copolymer CPA-1, x/y, was 90/10.

IR, ν (KBr, cm$^{-1}$) 3329 (N—H), 3070, 2936, 2860, 1719, 1630 (C=O), 1581, 1560, 1528, 1467, 1439, 1302, 1240 (P=O), 1200 (C—O—C), 1098, 1000, 960, 910, 824, 687.

The molecular weight of the copolymer CPA-1 was measured by GPC under the conditions described hereinabove, resulting in a number average molecular weight and a weight average molecular weight of 22×10$^5$ and 3.85×10$^5$, respectively. The copolymer CPA-1 did not have a glass transition temperature (softening point) in the range of 0 to 200° C. according to differential scanning calorimetry, and proved to be highly heat resistant.

<Synthesis of CPA-2>

In an argon atmosphere, the compound (6) from Example 1 (0.500 g, 0.789 mmol), hexamethylenediamine (0.214 g, 1.84 mmol) and sodium hydrogencarbonate (0.133 g, 1.58 mmol) were dissolved in distilled water (2.63 ml) in a three-necked flask. A solution of isophthalic acid chloride (0.534 g, 2.63 mmol) in chloroform (2.63 ml) was added dropwise to the solution over a period of 20 to 30 seconds to perform interfacial polycondensation. The resultant precipitate was sufficiently washed with methanol, suction filtered and dried under reduced pressure to give a polyamide copolymer with a phosphorylcholine group represented by Formula CPA-2 above as a brown solid (weight: 0.913 g, yield: 86.5%). The IR spectrum of the copolymer CPA-2 was identical to that of the copolymer CPA-1. From the $^1$H-NMR spectrum, the copolymerization ratio (on a molar basis) of the copolymer CPA-2, x/y, was 72/28.

The molecular weight of the copolymer CPA-2 was measured by GPC under the conditions described hereinabove, resulting in a number average molecular weight and a weight average molecular weight of 2.91×10$^5$ and 4.58×10$^5$, respectively. The copolymer CPA-2 did not have a glass transition temperature (softening point) in the range of 0 to 200° C. according to differential scanning calorimetry, and proved to be highly heat resistant.

<Synthesis of CPA-3>

In an argon atmosphere, the compound (6) from Example 1 (0.833 g, 1.32 mmol), hexamethylenediamine (0.153 g, 1.32 mmol) and sodium hydrogencarbonate (0.442 g, 5.26 mmol) were dissolved in distilled water (8.77 ml) in a three-necked flask. A solution of isophthalic acid chloride (0.534 g, 2.63 mmol) in chloroform (8.77 ml) was added dropwise to the solution over a period of 20 to 30 seconds to perform interfacial polycondensation. The resultant precipitate was sufficiently washed with methanol, suction filtered and dried under reduced pressure to give a polyamide copolymer with a phosphorylcholine group represented by Formula CPA-3 above as a brown solid (weight: 1.22 g, yield: 91.8%). The IR spectrum of the copolymer CPA-3 was identical to that of the copolymer CPA-1. From the $^1$H-NMR spectrum, the copolymerization ratio (on a molar basis) of the copolymer CPA-3, x/y, was 52/48.

The molecular weight of the copolymer CPA-3 was measured by GPC under the conditions described hereinabove, resulting in a number average molecular weight and a weight average molecular weight of 1.95×10$^5$ and 3.31×10$^5$, respectively. The copolymer CPA-3 did not have a glass transition temperature (softening point) in the range of 0 to 200° C. according to differential scanning calorimetry, and proved to be highly heat resistant.

The copolymers CPA-1, CPA-2 and CPA-3 were found to be soluble in N-methylpyrrolidinone and partly soluble in dimethylformamide, and to be insoluble in water, methanol, ethanol, chloroform, acetone, tetrahydrofuran and acetonitrile. The solubility of these copolymers in specific solvents provides advantageous forming processability in the material making such as coating and hollow filament production. Because of the insolubility in many other solvents, the materials may give super durable devices.

Separately, the copolymers CPA-1, CPA-2 and CPA-3 were each dissolved in N-methylpyrrolidinone and the solutions were each cast on a Teflon (registered trademark) substrate and were heated at 100° C. to evaporate the solvent. The resultant films from the copolymer solutions were excellent in rigidity.

Example 4

Synthesis 3 of Polymer (Copolymer) According to the Invention

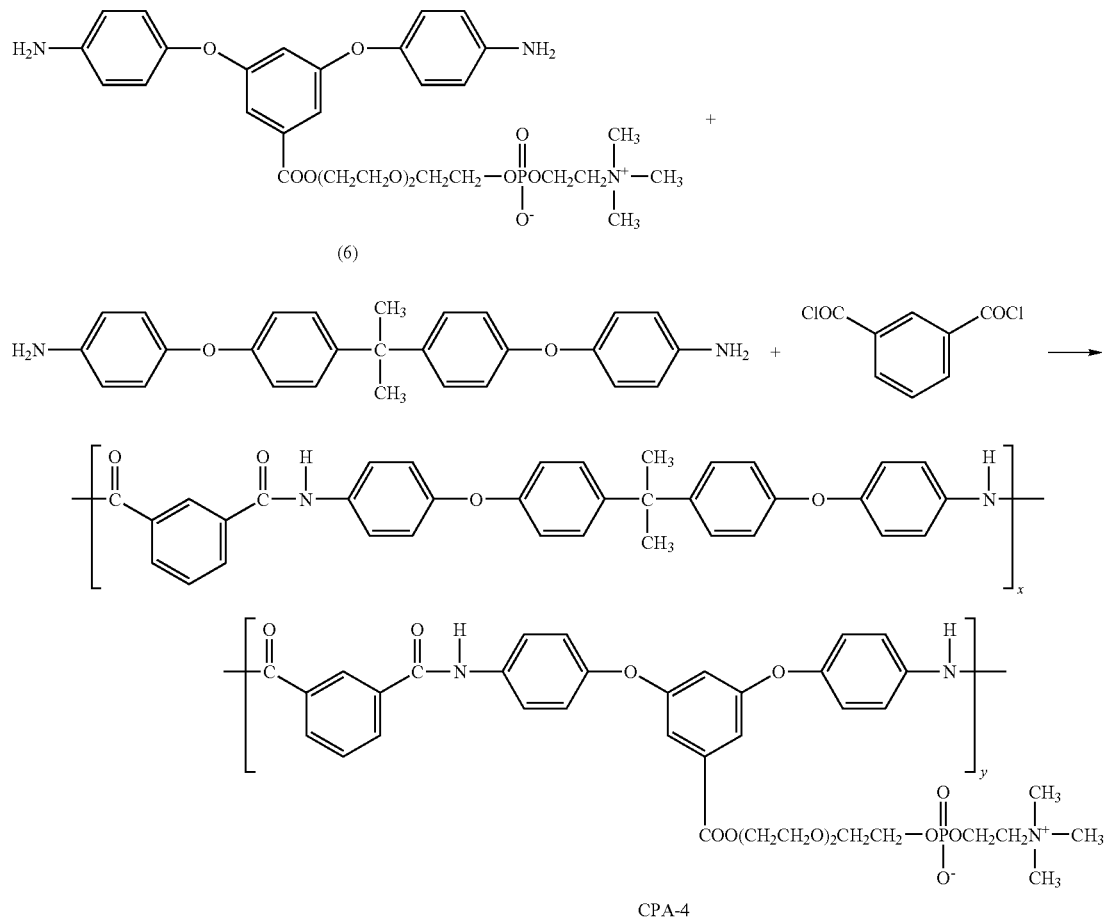

<Synthesis of CPA-4>

In an argon atmosphere, the compound (6) from Example 1 (0.500 g, 0.789 mmol), 2,2-bis[(4-(4-aminophenoxy)phenyl) propane (0.756 g, 1.84 mmol) and isophthalic acid chloride (0.534 g, 2.63 mmol) were mixed together in a three-necked flask. The mixture was cooled to −78° C., and N-methylpyrrolidinone (3.50 ml) was slowly added thereto. The mixture was then brought to room temperature and was stirred for 2 hours. The resultant polymer solution was poured into an excess of methanol. The precipitate was suction filtered and dried under reduced pressure to give a polyamide copolymer with a phosphorylcholine group represented by Formula CPA-4 above as a yellow solid (weight: 1.55 g, yield: 97.1%). The structure of the copolymer was determined from the IR spectrum given below. From the $^1$H-NMR spectrum, the copolymerization ratio (on a molar basis) of the copolymer CPA-4, x/y, was 72/28.

IR, ν (KBr, cm$^{-1}$): 3280 (N—H), 3030, 2950, 2872, 1719, 1653 (C=O), 1609, 1499, 1406, 1306, 1232 (P=O), 1203 (C—O—C), 1171, 1013, 831, 720.

The molecular weight of the copolymer CPA-1 was measured by GPC under the conditions described hereinabove, resulting in a number average molecular weight and a weight average molecular weight of $1.13 \times 10^5$ and $3.54 \times 10^5$, respectively. The copolymer CPA-4 did not have a glass transition temperature (softening point) in the range of 0 to 200° C. according to differential scanning calorimetry, and proved to be highly heat resistant.

The copolymer CPA-4 was found to be soluble in N-methylpyrrolidinone, dimethylformamide and dimethylsulfoxide, and insoluble in water, methanol, ethanol, chloroform, acetone, tetrahydrofuran and acetonitrile. The CPA-4's solubility in specific solvents provides advantageous forming processability in the material making such as coating and hollow filament production. Because of the insolubility in many other solvents, the materials may give super durable devices.

Separately, the copolymer CPA-4 was dissolved in N-methylpyrrolidinone and the solution was cast on a Teflon (registered trademark) substrate and was heated at 100° C. to evaporate the solvent. The resultant film was excellent in rigidity.

Example 5

Synthesis 4 of Polymer (Copolymer) According to the Invention

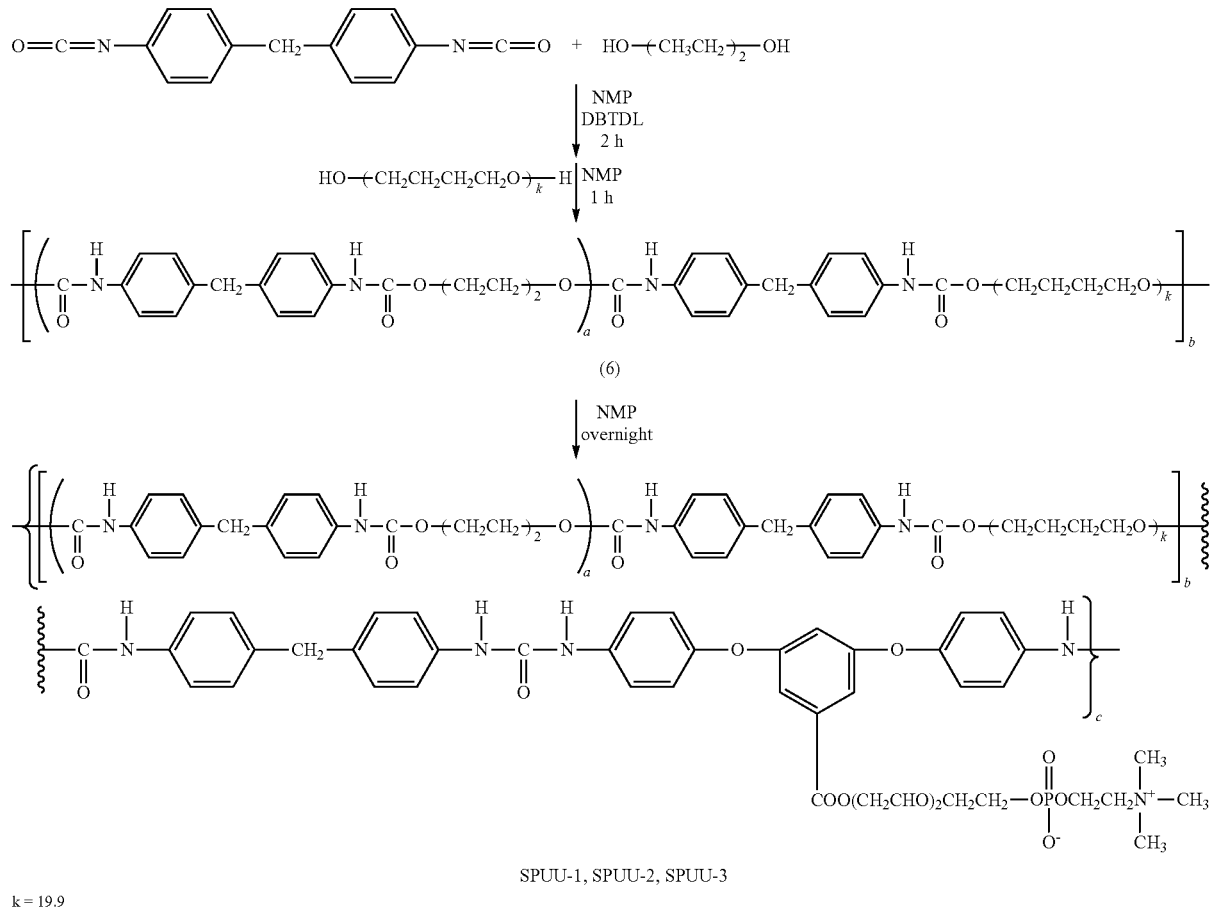

SPUU-1, SPUU-2, SPUU-3 k = 19.9

<Synthesis of SPUU-1>

In an argon atmosphere, 1,4-butanediol (0.350 ml, 4.00 mmol) and dibutyltin dilaurate (DBTDL) (0.2 ml) were dissolved in N-methylpyrrolidinone (NMP) (8.00 ml) in a three-necked flask. A solution of 4,4'-diphenylmethane diisocyanate (2.00 g, 7.99 mmol) in N-methylpyrrolidinone (8.00 ml) was slowly added dropwise to the solution at room temperature. After the completion of the dropwise addition, the solution was reacted at 50° C. for 2 hours. Thereafter, a solution of the compound (6) from Example 1 (0.844 g, 1.33 mmol) in N-methylpyrrolidinone (1.50 ml) was slowly added dropwise to the reaction solution at 0° C., followed by reaction at 0° C. for 0.5 hour. After the completion of the reaction, a solution of polytetramethylene glycol (2.66 g, 2.66 mmol) in N-methylpyrrolidinone (3.00 ml) was slowly added dropwise to the reaction solution at 0° C., followed by reaction at 50° C. overnight. The resultant reaction solution was poured into an excess of a solvent mixture (methanol:diethyl ether=1:1 (by volume)). The precipitate caused was suction filtered and dried under reduced pressure to give a segmented poly(urethane-urea) with a phosphorylcholine group represented by Formula SPUU-1 above as a white solid (weight: 4.81 g, yield: 82.1%). The structure of the polymer was determined from the IR spectrum given below. From the $^1$H-NMR spectrum, the phosphorylcholine group content in the polymer SPUU-1 was found to be 14.9 mol %.

IR, ν (KBr, cm$^{-1}$): 3325 (N—H), 3190, 2943, 2860, 2797, 1701 (C=O), 1599, 1533, 1506, 1413, 1310, 1230 (P=O), 1204 (C—O—C), 1065, 1016, 962, 816, 770.

Measurement of the molecular weight of the polymer SPUU-1 by GPC under the conditions described hereinabove gave two peaks. One peak corresponded to a number average molecular weight and a weight average molecular weight of $2.10 \times 10^5$ and $2.42 \times 10^5$, respectively. The other peak corresponded to a number average molecular weight and a weight average molecular weight of $0.22 \times 10^5$ and $0.38 \times 10^5$, respectively. The polymer SPUU-1 did not have a glass transition temperature (softening point) in the range of 0 to 200° C. according to differential scanning calorimetry, and proved to be highly heat resistant.

The polymer SPUU-1 was found to be soluble in N-methylpyrrolidinone, dimethylformamide, dimethylsulfoxide and tetrahydrofuran, and insoluble in water, methanol, ethanol, acetone, chloroform and acetonitrile. The SPUU-1's solubility in specific solvents provides advantageous forming processability in the material making such as coating and hollow filament production. Because of the insolubility in many other solvents, the materials may give super durable devices.

Separately, the polymer SPUU-1 was dissolved in N-methylpyrrolidinone and the solution was cast on a Teflon (registered trademark) substrate and was heated at 100° C. to evaporate the solvent. The resultant film was excellent in rigidity.

<Synthesis of SPUU-2>

In an argon atmosphere, 1,4-butanediol (0.240 g, 2.66 mmol) and dibutyltin dilaurate (0.2 ml) were dissolved in N-methylpyrrolidinone (7.00 ml) in a three-necked flask. A solution of 4,4'-diphenylmethane diisocyanate (2.00 g, 7.99 mmol) in N-methylpyrrolidinone (7.00 ml) was slowly added dropwise to the solution at room temperature. After the completion of the dropwise addition, the solution was reacted at 50° C. for 2 hours. Thereafter, a solution of the compound (6) from Example 1 (1.69 g, 2.66 mmol) in N-methylpyrrolidinone (3.00 ml) was slowly added dropwise to the reaction solution at 0° C., followed by reaction at 0° C. for 0.5 hour. After the completion of the reaction, a solution of polytetramethylene glycol (2.66 g, 2.66 mmol) in N-methylpyrrolidinone (3.00 ml) was slowly added dropwise to the reaction solution at 0° C., followed by reaction at 50° C. overnight. The resultant reaction solution was poured into an excess of a solvent mixture (methanol:diethyl ether=1:1 (by volume)). The precipitate caused was suction filtered and dried under reduced pressure to give a segmented poly(urethane-urea) with a phosphorylcholine group represented by Formula SPUU-2 above as a brown solid (weight: 5.09 g, yield: 77.2%). The structure of the polymer was determined from the IR spectrum given below. From the $^1$H-NMR spectrum, the phosphorylcholine group content in the polymer SPUU-2 was found to be 19.7 mol %.

Measurement of the molecular weight of the polymer SPUU-2 by GPC under the conditions described hereinabove gave two peaks. One peak corresponded to a number average molecular weight and a weight average molecular weight of $120 \times 10^5$ and $189 \times 10^5$, respectively. The other peak corresponded to a number average molecular weight and a weight average molecular weight of $0.29 \times 10^5$ and $0.47 \times 10^5$, respectively. The polymer SPUU-2 did not have a glass transition temperature (softening point) in the range of 0 to 200° C. according to differential scanning calorimetry, and proved to be highly heat resistant.

The polymer SPUU-2 was found to be soluble in N-methylpyrrolidinone, dimethylformamide, dimethylsulfoxide and tetrahydrofuran, and insoluble in water, methanol, ethanol, acetone, chloroform and acetonitrile. The SPUU-2's solubility in specific solvents provides advantageous forming processability in the material making such as coating and hollow filament production. Because of the insolubility in many other solvents, the materials may give super durable devices.

Separately, the polymer SPUU-2 was dissolved in N-methylpyrrolidinone and the solution was cast on a Teflon (registered trademark) substrate and was heated at 100° C. to evaporate the solvent. The resultant film was excellent in rigidity.

<Synthesis of SPUU-3>

In an argon atmosphere, 1,4-butanediol (0.120 g, 1.33 mmol) and dibutyltin dilaurate (0.2 ml) were dissolved in N-methylpyrrolidinone (6.50 ml) in a three-necked flask. A solution of 4,4'-diphenylmethane diisocyanate (2.00 g, 7.99 mmol) in N-methylpyrrolidinone (6.50 ml) was slowly added dropwise to the solution at room temperature. After the completion of the dropwise addition, the solution was reacted at 50° C. for 2 hours. Thereafter, a solution of the compound (6) from Example 1 (2.53 g, 4.00 mmol) in N-methylpyrrolidinone (4.00 ml) was slowly added dropwise to the reaction solution at 0° C., followed by reaction at 0° C. for 0.5 hour. After the completion of the reaction, a solution of polytetramethylene glycol (2.66 g, 2.66 mmol) in N-methylpyrrolidinone (3.00 ml) was slowly added dropwise to the reaction solution at 0° C., followed by reaction at 50° C. overnight. The resultant reaction solution was poured into an excess of a solvent mixture (methanol:diethyl ether=1:1 (by volume)) The precipitate caused was suction filtered and dried under reduced pressure to give a segmented poly(urethane-urea) with a phosphorylcholine group represented by Formula SPUU-3 above as a brown solid (weight: 4.72 g, yield: 64.6%). The structure of the polymer was determined from the IR spectrum given below. From the $^1$H-NMR spectrum, the phosphorylcholine group content in the polymer SPUU-3 was found to be 38.7 mol %.

Measurement of the molecular weight of the polymer SPUU-3 by GPC under the conditions described hereinabove gave two peaks. One peak corresponded to a number average molecular weight and a weight average molecular weight of $227 \times 10^5$ and $255 \times 10^5$, respectively. The other peak corresponded to a number average molecular weight and a weight average molecular weight of $0.14 \times 10^5$ and $0.20 \times 10^5$, respectively. The polymer SPUU-3 did not have a glass transition temperature (softening point) in the range of 0 to 200° C. according to differential scanning calorimetry, and proved to be highly heat resistant.

The polymer SPUU-3 was found to be soluble in N-methylpyrrolidinone, dimethylformamide, dimethylsulfoxide and tetrahydrofuran, and insoluble in water, methanol, ethanol, acetone, chloroform and acetonitrile. The SPUU-3's solubility in specific solvents provides advantageous forming processability in the material making such as coating and hollow filament production. Because of the insolubility in many other solvents, the materials may give super durable devices.

Separately, the polymer SPUU-3 was dissolved in N-methylpyrrolidinone and the solution was cast on a Teflon (registered trademark) substrate and was heated at 100° C. to evaporate the solvent. The resultant film was excellent in rigidity.

Example 6

Synthesis 2 of Diamine Compound According to the Invention

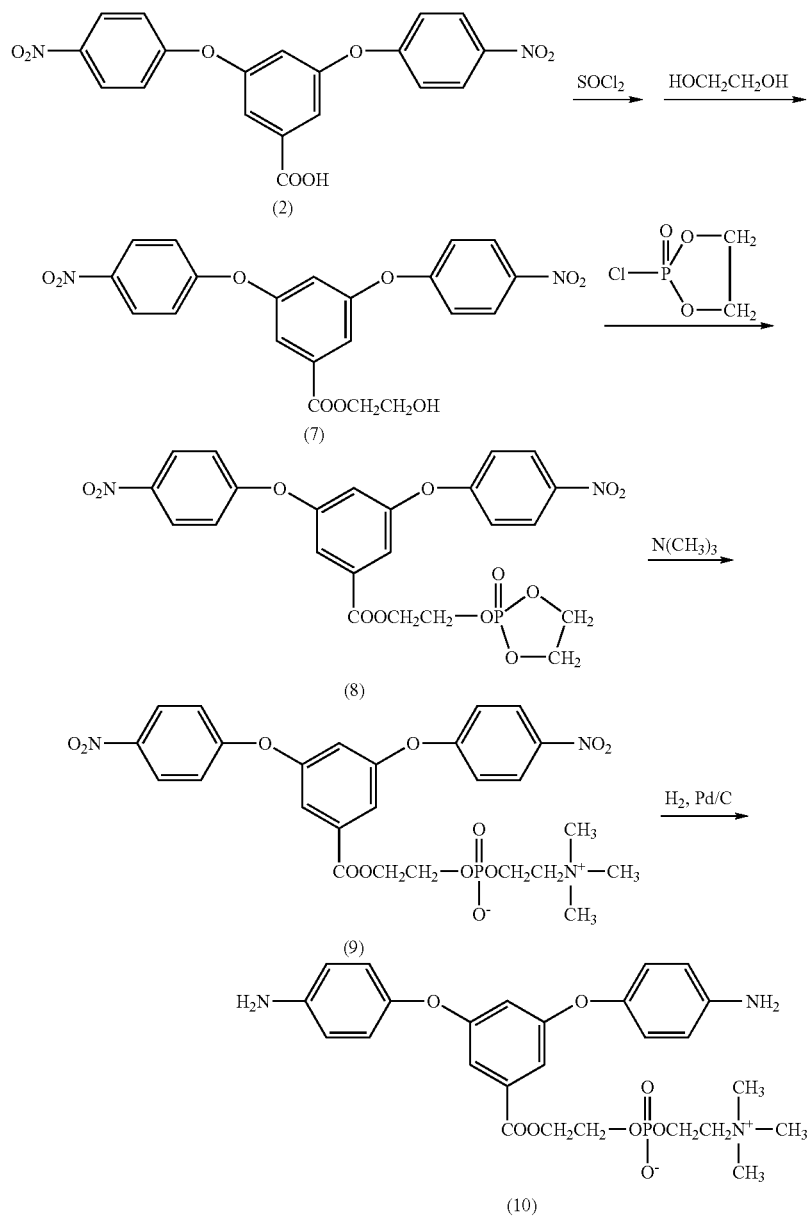

[Chem. 22]

<Synthesis of Compound (7)>

Under a stream of argon, the compound (2) from the reaction in Example 1 (14.7 g, 37.1 mmol), thionyl chloride (100 ml) and dimethylformamide (0.2 ml) were mixed and reacted together in a three-necked flask under reflux for 6 hours. The solvent was evaporated, and a white solid resulted. In an argon atmosphere, a solution of the white solid in dry tetrahydrofuran (130 ml) was slowly added dropwise to a three-necked flask which contained a solution of ethylene glycol (20.6 ml, 371 mmol), dry tetrahydrofuran (290 ml) and dry triethylamine (10.3 ml, 74.2 mmol), with the flask in an ice water bath. After the completion of the dropwise addition, the mixture was stirred at room temperature overnight. Subsequently, the reaction solution was extracted with chloroform and the extract was washed with distilled water. The organic phase was dehydrated with sodium sulfate and then filtered, and the solvent was distilled away under reduced pressure. Thereafter, the distillate was purified by silica gel column chromatography (developing solvents: hexane/ethyl acetate=1/2 (by volume)) to give an alcohol compound represented by Formula (7) above as a yellow liquid (weight: 9.18 g, yield: 56.0%). The structure of the compound was determined from the $^1$H-NMR and IR spectra given below:

$^1$H-NMR, δ (400 MHz, DMSO-$d_6$, ppm): 8.27 (4H, d, J=9.27 Hz), 7.63 (2H, d, J=1.95 Hz), 7.29 (1H, s), 7.26 (4H, d, J=9.27 Hz), 4.93 (1H, t, J=5.61 Hz), 4.29 (2H, t, J=4.63 Hz), 3.70 (2H, q, J=5.04 Hz).

IR, ν (KBr, cm⁻¹): 3385 (—OH), 3100, 3082, 2985, 2939, 1728 (C=O), 1581, 1514, 1489 (—NO$_2$), 1447, 1350 (—NO$_2$), 1300, 1234, 1215 (C—O—C), 1165, 1113, 1076, 1001, 968, 895, 851, 750.

<Synthesis of Compound (8)>

In an argon atmosphere, the compound (7) from the above reaction (9.00 g, 20.4 mmol), dry tetrahydrofuran (110 ml) and dry triethylamine (11.3 g, 81.7 mmol) were mixed together in a three-necked flask. While stirring was performed with the flask in an ice water bath, 2-chloro-2-oxo-1,3,2-dioxaphosphorane (3.75 ml, 40.9 mmol) was slowly added dropwise. After the completion of the dropwise addition, the mixture was stirred at room temperature for 2 hours. Subsequently, the reaction solution was extracted with chloroform and the extract was washed with distilled water. The organic phase was dehydrated with sodium sulfate and then filtered, and the solvent was distilled away under reduced pressure. As a result, a phosphorane compound represented by Formula (8) above was obtained as a brown liquid (weight: 10.9 g, yield: 97.7%). The structure of the compound was determined from the ¹H-NMR spectrum given below:

¹H-NMR, δ (400 MHz, DMSO-d$_6$, ppm): 8.28 (4H, d, J=9.27 Hz), 7.60 (2H, s), 7.27 (1H, s), 7.25 (4H, m), 4.47 (2, d, J=4.89 Hz), 4.36 (6H, m).

<Synthesis of Compound (9)>

In an argon atmosphere, the compound (8) from the above reaction (10.9 g, 20.0 mmol) was dissolved in dry acetonitrile (130 ml) in an evaporation flask. Trimethylamine (3.54 ml, 39.9 mmol) was added to the solution in an ice water bath, and the flask was tightly closed. Reaction was carried out at 60° C. overnight, and the solvent was distilled away under reduced pressure. As a result, a dinitro compound with a phosphorylcholine group represented by Formula (9) above was obtained as a white solid (weight: 11.3 g, yield: 93.1%). The structure of the compound was determined from the ¹H-NMR and IR spectra given below:

¹H-NMR, δ (400 MHz, DMSO-d$_6$, ppm): 8.27 (4H, d, J=9.27 Hz), 7.58 (2H, d, J=2.44 Hz), 7.27 (4H, d, J=9.27 Hz), 7.22 (1H, m), 4.42 (2H, s), 4.10 (2H, s), 4.01 (2H, s), 3.59 (2H, s), 3.16 (9H, s).

IR, ν (KBr, cm⁻¹): 3120, 3080, 2950, 2855, 1719 (C=O), 1580, 1518, 1489 (—NO$_2$), 1445, 1344 (—NO$_2$), 1304, 1238 (P=O), 1211 (C—O—C), 1167, 1078, 999, 968, 860, 750.

<Synthesis of Compound (10)>

The compound (9) from the above reaction (11.3 g, 18.6 mmol) was dissolved in a solvent mixture (methanol:tetrahydrofuran=1:1 (by volume)) (203 ml) in an evaporation flask. To the solution, 5% palladium-containing carbon powder (0.787 g, 0.372 mmol) was added, and the mixture was cooled to about −80° C. in an acetone-dry ice bath. The flask was purged with hydrogen, and reaction was carried out at room temperature overnight. The reaction solution was filtered through Celite. The filtrate was distilled under reduced pressure to approximately half the volume, and was poured into diethyl ether. The resultant precipitate was suction filtered and was dried under reduced pressure to afford a diamine compound with a phosphorylcholine group represented by Formula (10) above as a yellow solid (weight: 3.72 g, yield: 36.7%). The structure of the compound was determined from the ¹H-NMR and IR spectra given below:

¹H-NMR, δ (400 MHz, DMSO-d$_6$, ppm): 7.02 (2H, d, J=1.95 Hz), 6.78 (4H, d, J=8.78 Hz), 6.61 (1H, s), 6.58 (4H, m), 4.33 (2H, t, J=4.88 Hz), 4.06 (2H, s), 3.94 (2H, t, J=5.12 Hz), 3.52 (2H, t, J=4.63 Hz), 3.15 (9H, s).

IR, ν (KBr, cm⁻¹): 3219 (—NH$_2$), 2972, 2885, 1717 (C=O), 1595, 1506, 1443, 1308, 1240 (P=O), 1209 (C—O—C), 1124, 1086, 1003, 953, 839, 768.

Example 7

Synthesis 5 of Polymer (Copolymer) According to the Invention

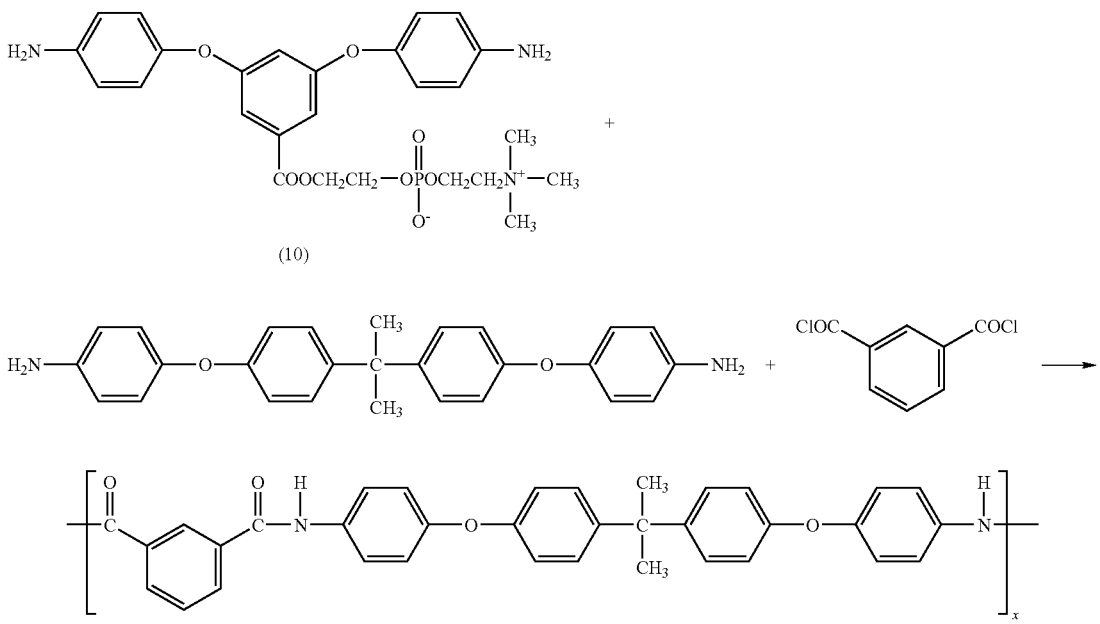

-continued

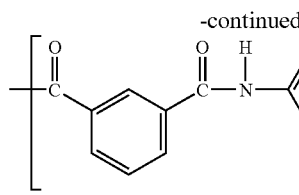 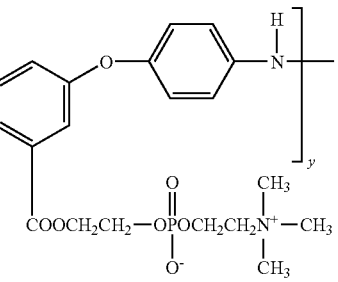

CPA-5, CPA-6, CPA-7

<Synthesis of CPA-5>

In an argon atmosphere, the compound (10) from Example 6 (0.403 g, 0.739 mmol), 2,2-bis[(4-(4-aminophenoxy)phenyl)propane (0.706 g, 1.72 mmol) and isophthalic acid chloride (0.500 g, 2.46 mmol) were mixed together in a three-necked flask. The mixture was cooled to −78° C., and N-methylpyrrolidinone (3.28 ml) was slowly added thereto. The mixture was then brought to room temperature and was stirred overnight. The resultant polymer solution was poured into an excess of methanol. The precipitate was suction filtered and dried under reduced pressure to give a polyamide copolymer with a phosphorylcholine group represented by Formula CPA-5 above as a yellow solid (weight: 1.31 g, yield: 91.8%). The structure of the copolymer was determined from the IR spectrum given below. From the $^1$H-NMR spectrum, the copolymerization ratio (on a molar basis) of the copolymer CPA-5, x/y, was 76/24.

IR, ν (KBr, cm$^{-1}$): 3308 (N—H), 3130, 2970, 2872, 1725, 1655 (C=O), 1603, 1499, 1406, 1308, 1229 (P=O), 1208 (C—O—C), 1172, 1013, 831, 723.

The molecular weight of the copolymer CPA-5 was measured by GPC under the conditions described hereinabove, resulting in a number average molecular weight and a weight average molecular weight of $1.8 \times 10^5$ and $7.4 \times 10^5$, respectively. The copolymer CPA-5 did not have a glass transition temperature (softening point) in the range of 0 to 200° C. according to differential scanning calorimetry, and proved to be highly heat resistant.

The copolymer CPA-5 was found to be soluble in N-methylpyrrolidinone, dimethylformamide and dimethylsulfoxide, partly soluble in tetrahydrofuran and chloroform, and insoluble in water, methanol, ethanol, acetone and acetonitrile. The CPA-5's solubility in specific solvents provides advantageous forming processability in the material making such as coating and hollow filament production. Because of the insolubility in many other solvents, the materials may give super durable devices.

Separately, the copolymer CPA-5 was dissolved in N-methylpyrrolidinone and the solution was cast on a Teflon (registered trademark) substrate and was heated at 100° C. to evaporate the solvent. The resultant film was excellent in rigidity.

<Synthesis of CPA-6>

In an argon atmosphere, the compound (10) from Example 6 (0.670 g, 1.23 mmol), 2,2-bis[(4-(4-aminophenoxy)phenyl)propane (0.505 g, 1.23 mmol) and isophthalic acid chloride (0.500 g, 2.46 mmol) were mixed together in a three-necked flask. The mixture was cooled to −78° C., and N-methylpyrrolidinone (4.46 ml) was slowly added thereto. The mixture was then brought to room temperature and was stirred overnight. The resultant polymer solution was poured into an excess of methanol. The precipitate was suction filtered and dried under reduced pressure to give a polyamide copolymer with a phosphorylcholine group represented by Formula CPA-6 above as a yellow solid (weight: 1.34 g, yield: 89.7%). The structure of the copolymer was determined from the IR spectrum given below. From the $^1$H-NMR spectrum, the copolymerization ratio (on a molar basis) of the copolymer CPA-6, x/y, was 54/46.

The molecular weight of the copolymer CPA-6 was measured by GPC under the conditions described hereinabove, resulting in a number average molecular weight and a weight average molecular weight of $5.8 \times 10^5$ and $12 \times 1^5$ r respectively. The copolymer CPA-6 did not have a glass transition temperature (softening point) in the range of 0 to 200° C. according to differential scanning calorimetry, and proved to be highly heat resistant.

The copolymer CPA-6 was found to be soluble in N-methylpyrrolidinone, dimethylformamide and dimethylsulfoxide, partly soluble in tetrahydrofuran and chloroform, and insoluble in water, methanol, ethanol, acetone and acetonitrile. The CPA-6's solubility in specific solvents provides advantageous forming processability in the material making such as coating and hollow filament production. Because of the insolubility in many other solvents, the materials may give super durable devices.

Separately, the copolymer CPA-6 was dissolved in N-methylpyrrolidinone and the solution was cast on a Teflon (registered trademark) substrate and was heated at 100° C. to evaporate the solvent. The resultant film was excellent in rigidity.

<Synthesis of CPA-7>

In an argon atmosphere, the compound (10) from Example 6 (0.753 g, 1.38 mmol), 2,2-bis[(4-(4-aminophenoxy)phenyl)propane (0.243 g, 0.590 mmol) and isophthalic acid chloride (0.400 g, 1.97 mmol) were mixed together in a three-necked flask. The mixture was cooled to −78° C., and N-methylpyrrolidinone (3.58 ml) was slowly added thereto. The mixture was then brought to room temperature and was stirred overnight. The resultant polymer solution was poured into an excess of methanol. The precipitate was suction filtered and dried under reduced pressure to give a polyamide copolymer with a phosphorylcholine group represented by Formula CPA-7 above as a yellow solid (weight: 0.680 g, yield: 54.5%). The structure of the copolymer was determined from the IR spectrum given below. From the $^1$H-NMR spectrum, the copolymerization ratio (on amolar basis) of the copolymer CPA-7, x/y, was 46/54.

The molecular weight of the copolymer CPA-7 was measured by GPC under the conditions described hereinabove, resulting in a number average molecular weight and a weight average molecular weight of $5.9 \times 10^5$ and $12 \times 10^5$ respectively. The copolymer CPA-7 did not have a glass transition temperature (softening point) in the range of 0 to 200° C. according to differential scanning calorimetry, and proved to be highly heat resistant.

The copolymer CPA-7 was found to be soluble in N-methylpyrrolidinone, dimethylformamide and dimethylsulfoxide, partly soluble in tetrahydrofuran and chloroform, and insoluble in water, methanol, ethanol, acetone and acetonitrile. The CPA-7's solubility in specific solvents provides advantageous forming processability in the material making such as coating and hollow filament production. Because of the insolubility in many other solvents, the materials may give super durable devices.

Separately, the copolymer CPA-7 was dissolved in N-methylpyrrolidinone and the solution was cast on a Teflon (registered trademark) substrate and was heated at 100° C. to evaporate the solvent. The resultant film was excellent in rigidity.

Test Example 1

Blood-contact Test for Polymer Membranes

The polymers PA-1, CPA-1, CPA-2, CPA-3, CPA-4, CPA-5, CPA-6 and CPA-7 produced in Examples 2, 3, 4 and 7 were each dissolved in N-methylpyrrolidinone to give respective 0.5 wt % polymer solutions.

Circular polyethyleneterephthalate (PET) substrates (diameter: 14 mm, thickness: 0.2 mm) were soaked in the solutions and coated in a wet environment at 60° C. over a period of 2 hours. These procedures were performed two times, and respective polymer membranes were formed on the PET substrates, thereby producing test pieces.

Separately, the polymers SPUU-1, SPUU-2 and SPUU-3 obtained in Example 5 were each dissolved in N-methylpyrrolidinone, and the solutions (concentration: 2.0 wt %) were cast to form membranes. Circular test pieces (diameter: 14 mm, thickness: 0.2 mm) were cut out from the polymer membranes.

These test pieces were soaked in a phosphate buffer solution (pH=7.4) at room temperature over a period of 24 hours. After removal of the phosphate buffer solution, the test pieces were soaked in 700 μl of human platelet rich plasma (PRP) from human blood over a period of 1 hour at 37° C. The surface of the polymer membrane test pieces was washed five times with a phosphate buffer solution (pH=7.4). Subsequentlyr the test pieces were soaked in an aqueous Triton solution (nonionic surfactant) for 1 hour and thereby PRP that had been adsorbed on the polymer membrane surface was desorbed therefrom into the solution.

Cytotoxic agent LDH (lactate dehydrogenase) was added to the solutions, and reaction with dehydrogenase was performed. Thereafter, the absorbance at 570 nm of the solutions was measured with a microplate reader.

Separately, the human platelet rich plasma (PRP) and solutions thereof in a phosphate buffer solution (pH=7.4) having stepwise decreasing concentrations were analyzed on a cell count device (Coulter counter) (MULTISIZER II, Beckman Counter, Calif.) to determine the platelet concentration. They were then measured for absorbance as described above, and a calibration curve was prepared. The amounts of platelets adsorbed on the polymer membrane test pieces were determined based on the calibration curve.

The amounts of platelets adsorbed on the surface of PA-1, CPA-1, CPA-2, CPA-3, CPA-4, CPA-5, CPA-6, CPA-7, SPUU-1, SPUU-2 and SPUU-3 were $7.06 \times 10^4$ (cells/cm$^2$), $1.70 \times 10^4$ (cells/cm$^2$), $2.57 \times 10^4$ (cells/cm$^2$), $1.65 \times 10^4$ (cells/cm$^2$), $5.74 \times 10^4$ (cells/cm$^2$), $2.20 \times 10^4$ (cells/cm$^2$), $1.53 \times 10^4$ (cells/cm$^2$), $1.13 \times 10^4$ (cells/cm$^2$), $0.290 \times 10^4$ (cells/cm$^2$), $0.172 \times 10^4$ (cells/cm$^2$) and $0.0925 \times 10^4$ (cells/cm$^2$), respectively.

Test Example 2

Measurement of Mechanical Strength of Segmented Poly(Urethane-urea) Films

The polymers ,SPUU-1, SPUU-2 and SPUU-3 from Example 5 were each dissolved in N-methylpyrrolidinone, and the solutions (concentration: 2.0 wt %) were cast to form membranes. The membranes were then cut to a rectangular shape (length: 50 mm, width: 15 mm, thickness: 0.2 mm) to give polymer membrane test pieces. The test pieces were mounted on tensile tester LSC-1/300-SS-120S-L manufactured by TOKYO TESTING MACHINE and were stretched at a tensile rate of 12 mm/min, thereby obtaining a stress-strain curve for each shown in the drawing.

From FIG. 1, the tensile elastic moduli of the polymers SPUU-1, SPUU-2 and SPUU-3 are 31.6 MPa, 82.0 MPa and 267 MPa, respectively; the breaking strengths were 29.6 MPa, 19.8 MPa and 21.8 MPa, respectively; and the maximum elongations were 645%, 442% and 255%, respectively. The segmented poly(urethane-urea) polymers were demonstrated to give rigid films having superior mechanical strength.

Comparative Example 1

Synthesis and Blood-contact Test for Polyamide Having no Phosphorylcholine Group

[Chem. 24]

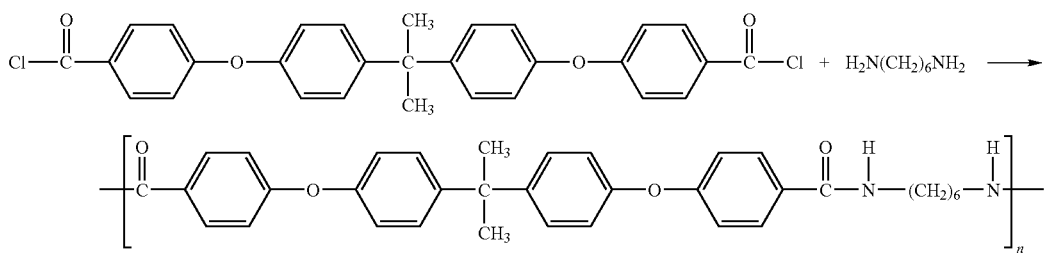

PA-2

<Synthesis of PA-2>

In an argon atmosphere, hexamethylenediamine (0.230 g, 1.98 mmol) and sodium hydrogencarbonate (0.333 g, 3.98 mmol) were dissolved in distilled water (6.60 ml) in a three-necked flask. A solution of 2,2-bis[(4-(4-chlorocarbonylphenoxy)phenyl)propane (1.00 g, 1.98 mmol) in chloroform (6.60 ml) was added dropwise to the solution over a period of 20 to 30 seconds to perform interfacial polycondensation. The resultant precipitate was sufficiently washed with methanol, suction filtered and dried under reduced pressure to give a polyamide represented by Formula PA-2 above as a white solid (weight: 0.756 g, yield: 61.4%). The structure of the polymer was determined from the IR spectrum given below:

IR, ν (KBr, cm$^{-1}$): 3327 (N—H), 3070, 3035, 2972, 2930, 2856, 1718, 1638 (C=O), 1597, 1545, 1491, 1236, 1169, 1100, 1080, 1013, 875, 833, 764.

The molecular weight of the polymer PA-2 was measured by GPC under the conditions described hereinabove, resulting in a number average molecular weight and a weight average molecular weight of $5.45 \times 10^4$ and $1.23 \times 10^5$, respectively. The polymer PA-2 did not have a glass transition temperature (softening point) in the range of 0 to 200° C. according to differential scanning calorimetry.

The polymer PA-2 was found to be soluble in aprotic polar solvents such as N-methylpyrrolidinone, dimethylformamide and dimethylsulfoxide, partly soluble in acetone, and insoluble in water, methanol, ethanol, chloroform, tetrahydrofuran and acetonitrile.

<Blood-contact Test for Polymer Membrane>

The polymer PA-2 from Comparative Example 1 formed a polymer membrane on a circular PET substrate to give a test piece in the same manner as in Test Examples. The test piece was brought into contact with PRP and the platelet amount on the polymer membrane test piece was determined.

The platelet amount on the PA-2 membrane surface was $8.48 \times 10^5$ (cells/cm$^2$).

This result shows that the PA-2 membrane adsorbed platelets more than 10 times as much as platelets adsorbed on PA-1, CPA-1, CPA-2, CPA-3, CPA-4, CPA-5, CPA-6, CPA-7, SPUU-1, SPUU-2 and SPUU-3. Accordingly, the polymers PA-1, CPA-1, CPA-2, CPA-3, CPA-4, CPA-5, CPA-6, CPA-7, SPUU-1, SPUU-2 and SPUU-3 having a phosphorylcholine group were demonstrated to have excellent antithrombotic activity compared to the polymer PA-2 having no phosphorylcholine group.

Comparative Example 2

Synthesis of Polyamide Having Phosphorylcholine Group But Differing in Structure

[Chem. 25]

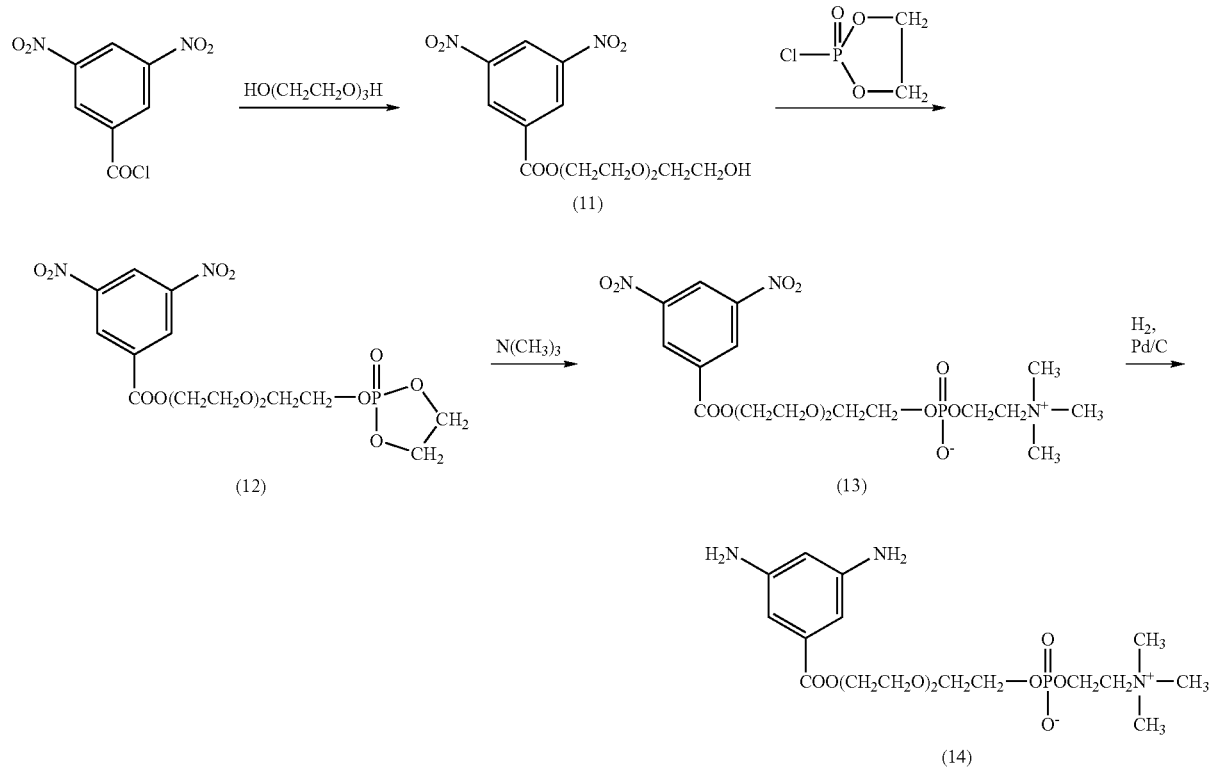

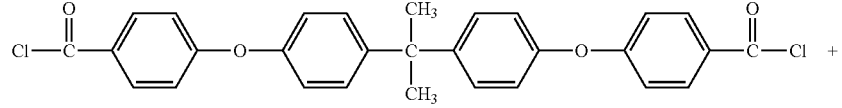

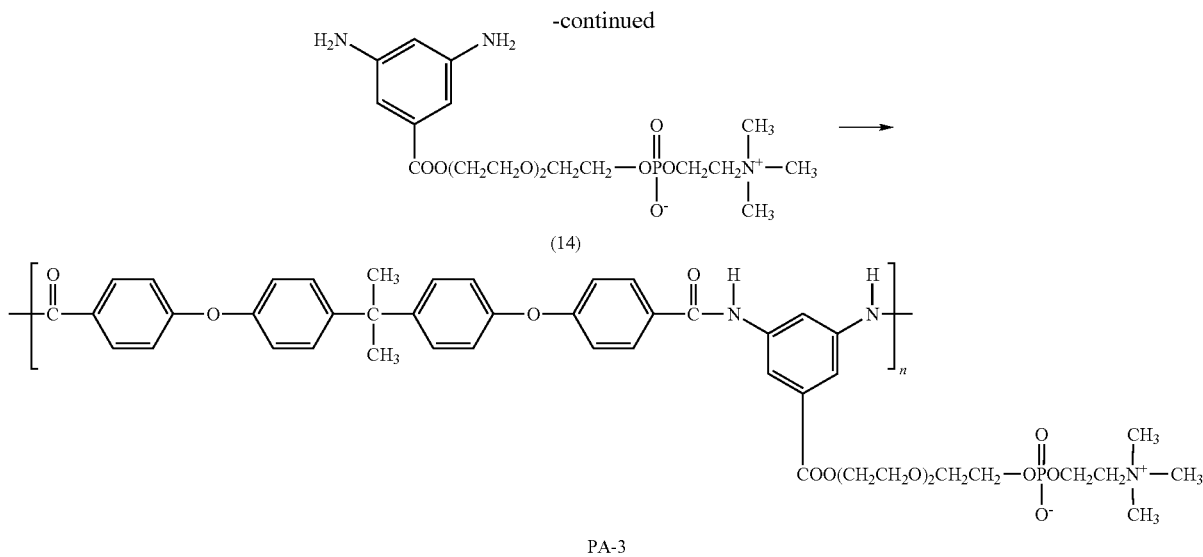

PA-3

<Synthesis of Compound (11)>

In an argon atmosphere, a solution of 3,5-dinitrobenzoyl chloride (10.0 g, 43.4 mmol) in dry tetrahydrofuran (150 ml) was slowly added dropwise to a three-necked flask which contained a solution of triethylene glycol (59.0 ml, 440 mmol), dry tetrahydrofuran (350 ml) and dry triethylamine (10.0 ml), with the flask in an ice water bath. After the completion of the dropwise addition, the mixture was stirred at room temperature overnight. Subsequently, the reaction solution was extracted with chloroform and the extract was washed with distilled water. The organic phase was dehydrated with sodium sulfate and then filtered, and the solvent was distilled away under reduced pressure. Thereafter, the distillate was purified by silica gel column chromatography (developing solvents: hexane/ethyl acetate=1/2 (by volume)) to give an alcohol compound represented by Formula (11) above as a yellow liquid (weight: 10.6 g, yield: 71.2%). The structure of the compound was determined from the $^1$H-NMR and IR spectra given below:

$^1$H-NMR, δ (400 MHz, CDCl$_3$, ppm): 9.23 (1H, m), 9.21 (2H, m), 4.63 (2H, t, J=4.39 Hz), 3.90 (2H, t, J=4.39 Hz), 3.73 (6H, m), 3.63 (2H, t, J=6.35 Hz), 2.42 (1H, bs).

IR, ν (KBr, cm$^{-1}$): 3223 (—OH), 3047, 2885, 1717 (C=O), 1628, 1595, 1540, 1490 (—NO$_2$), 1331, 1172, 1079, 845, 723.

<Synthesis of Compound (12)>

In an argon atmosphere, the compound (11) from the above reaction (4.75 g, 13.8 mmol), dry tetrahydrofuran (65 ml) and dry triethylamine (2.90 ml) were mixed together in a three-necked flask. While stirring was performed with the flask in an ice water bath, 2-chloro-2-oxo-1,3,2-dioxaphosphorane (1.90 ml, 20.7 mmol) was slowly added dropwise. After the completion of the dropwise addition, the mixture was stirred at room temperature for 2 hours. Subsequently, the reaction solution was extracted with chloroform and the extract was washed with distilled water. The organic phase was dehydrated with sodium sulfate and then filtered, and the solvent was distilled away under reduced pressure. As a result, a phosphorane compound represented by Formula (12) above was obtained as a brown liquid (weight: 4.85 g, yield: 78.1%). The structure of the compound was determined from the $^1$H-NMR and IR spectra given below:

$^1$H-NMR, δ (400 MHz, CDCl$_3$, ppm): 9.23 (1H, d, J=2.22 Hz), 8.96 (2H, d, J=2.20 Hz), 4.61 (2H, m), 4.45-4.29 (4H, m), 4.16 (2H, m), 3.91 (2H, m), 3.73 (6H, m).

IR, ν (KBr, cm$^{-1}$): 3100, 2975, 2882, 1732 (C=O), 1630, 1598, 1549, 1462 (—NO$_2$), 1346 (—NO$_2$), 1281, 1250 (P=O), 1030, 928, 845, 758.

<Synthesis of Compound (13)>

In an argon atmosphere, the compound (12) from the above reaction (4.85 g, 10.8 mmol) was dissolved in dry acetonitrile (30 ml) in an evaporation flask. Trimethylamine (1.90 ml, 21.5 mmol) was added to the solution in an ice water bath, and the flask was tightly closed. Reaction was carried out at 60° C. overnight, and the solvent was distilled away under reduced pressure. As a result, a dinitro compound with a phosphorylcholine group represented by Formula (13) above was obtained as a brown liquid (weight: 4.48 g, yield: 81.6%). The structure of the compound was determined from the $^1$H-NMR and IR spectra given below:

$^1$H-NMR, δ (400 MHz, DMSO-d$_6$, ppm): 9.08 (1H, t, J=1.95 Hz), 8.97 (2H, d, J=2.19 Hz), 4.55 (2H, m), 4.11 (2H, m), 3.84 (2H, m), 3.77 (2H, m), 3.64 (2H, m), 3.53-3.59 (6H, m), 3.18 (9H, s).

IR, ν (KBr, cm$^1$): 3101, 2940, 2883, 1734 (C=O), 1629, 1544, 1490 (—NO$_2$), 1458, 1348 (—NO$_2$), 1283, 1245 (P=O), 1173, 1090, 964, 924, 773.

<Synthesis of Compound (14)>

The compound (13) from the above reaction (4.45 g, 8.73 mmol) was dissolved in ethanol (60 ml) in an evaporation flask. To the solution, 5% palladium-containing carbon powder (0.450 g, 0.190 mmol) was added, and the mixture was cooled to about −80° C. in an acetone-dry ice bath. The flask was purged with hydrogen, and reaction was carried out at room temperature overnight. The reaction solution was filtered through Celite. The filtrate was distilled under reduced pressure to approximately half the volume, and was poured into diethyl ether. The resultant precipitate was suction filtered and was dried under reduced pressure to afford a diamine compound with a phosphorylcholine group represented by Formula (14) above as a yellow solid (weight: 2.12 g, yield: 54.1%). The structure of the compound was determined from the $^1$H-NMR and IR spectra given below:

$^1$H-NMR, δ (400 MHz, DMSO-d$_6$, ppm): 8.00 (1H, m), 7.79 (2H, m), 4.45 (2H, m), 4.35 (4H, s), 4.10 (2H, m), 3.77 (4H, m), 3.53-3.61 (8H, m), 3.15 (9H, s).

IR, ν (KBr, cm⁻¹): 3198 (—NH₂), 2950, 2887, 1722 (C=O), 1535, 1458, 1352, 1302, 1229 (P=O), 1059, 964, 775.

<Synthesis of PA-3>

In an argon atmosphere, the compound (14) from Comparative Example 2 (0.890 g, 1.98 mmol) and sodium hydrogencatbonate (0.335 g, 3.98 mmol) were dissolved in distilled water (6.59 ml) in a three-necked flask. A solution of 2,2-bis [(4-(4-chlorocarbonylphenoxy)phenyl)propane (1.00 g, 1.98 mmol) in chloroform (6.59 ml) was added dropwise to the solution over a period of 20 to 30 seconds to perform interfacial polycondensation. The resultant precipitate was sufficiently washed with acetone, suction filtered and dried under reduced pressure to give a polyamide with a phosphorylcholine group represented by Formula PA-3 above as a brown solid (weight: 0.892 g, yield: 47.2%). The structure of the polymer was determined from the IR spectrum given below:

IR, ν (KBrr cm⁻¹) 3414 (N—H), 2914, 1650 (C=O), 1624, 1541, 1452, 1354, 1296, 1236 (P=O), 1167, 1100, 1047, 966, 833, 791.

The molecular weight of the polymer PA-3 was measured by GPC under the conditions described hereinabove, resulting in a number average molecular weight and a weight average molecular weight of $6.09 \times 10^3$ and $2.01 \times 10^4$, respectively.

The polymer PA-3 was found to be soluble in aprotic polar solvents such as N-methylpyrrolidinone, dimethylformamide and dimethylsulfoxide, water and alcohol solvents such as methanol and ethanol, partly soluble in acetone and acetonitrile, and insoluble in tetrahydrofuran and chloroform.

Because the polymer PA-3 had a very low molecular weight compared to the polymer PA-1 from Example 2 and the production of membranes therefrom was difficult and further because the polymer was soluble in water, the blood-contact test was infeasible.

The invention claimed is:

1. A diamine compound having a phosphorylcholine group, represented by Formula (I):

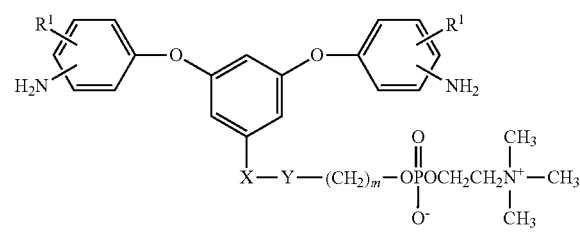

(I)

wherein two $R^1$ may be the same or different from each other and are each a hydrogen atom or a C1-6 alkyl group; X is a single bond, an oxygen atom, —COO—, —OOC—, —CONH—, —NH—, —NHCO—, —NR²— or —CH₂O—; Y is a single bond, a C1-6 alkylene group or an oligooxyalkylene group; $R^2$ is a C1-6 alkyl group; and m is an integer of 1 to 6.

2. A polymer which comprises at least 1 mol % of a structural unit with a phosphorylcholine group represented by Formula (II) below and has a number average molecular weight of not less than 5,000:

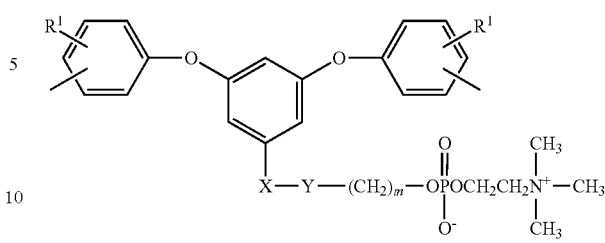

(II)

wherein two $R^1$ may be the same or different from each other and are each a hydrogen atom or a C1-6 alkyl group; X is a single bond, an oxygen atom, —COO—, —OOC—, —CONH—, —NH—, —NHCO—, —NR²— or —CH₂O—; Y is a single bond, a C1-6 alkylene group or an oligooxyalkylene group; $R^2$ is a C1-6 alkyl group; and m is an integer of 1 to 6.

3. The polymer according to claim 2, which has an amide bond, a urethane bond, a urea bond or an imide bond in its main chain skeleton.

4. A process for producing the polymer according to claim 2, which comprises,
polycondensation or polyaddition reaction of a diamine compound having a phosphorylcholine group represented by Formula (I) below with another polymerizable monomer, or
reacting the diamine compound having a phosphorylcholine group represented by Formula I with a functional group-terminated prepolymer capable of reacting with the diamine compound having a phosphorylcholine group represented by Formula (I):

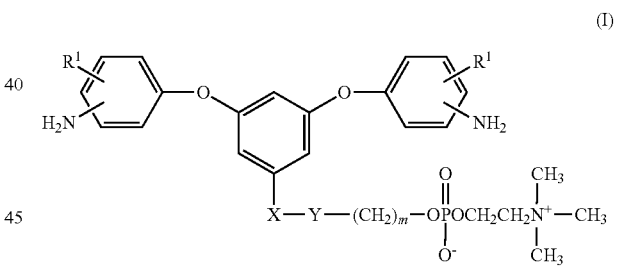

(I)

wherein two $R^1$ may be the same or different from each other and are each a hydrogen atom or a C1-6 alkyl group; X is a single bond, an oxygen atom, —COO—, —OOC—, —CONH—, —NH—, —NHCO—, —NR²— or —CH₂O—; Y is a single bond, a C1-6 alkylene group or an oligooxyalkylene group; $R^2$ is a C1-6 alkyl group; and m is an integer of 1 to 6.

5. The process according to claim 4, wherein another polymerizable monomer is at least one monomer selected from dicarboxylic acids, dicarboxylic acid derivatives, tetracarboxylic dianhydrides and diisocyanate compounds.

6. The process according to claim 4, wherein the functional group-terminated prepolymer is an isocyanate group-terminated urethane prepolymer obtained by reacting a diisocyanate compound and a diol compound.

7. The process according to claim 4, wherein,
at least one diamine compound having no phosphoryleholine group is co-present in the polycondensation or polyaddition reaction of the diamine compound having a phosphorylcholine group represented by Formula (I) with another polymerizable monomer, or at least one other diamine compound having no phosphorylcholine group is co-present in the reaction of the diamine compound having a phosphorylcholine group represented by Formula (I) with the functional group-terminated prepolymer.

8. The process according to claim 5, wherein, at least one other diamine compound having no phosphorylcholine group is co-present in the polycondensation or polyaddition reaction of the diamine compound having a phosphorylcholine group represented by Formula (I) with another polymerizable monomer, or at least one other diamine compound having no phosphorylcholine group is co-present in the reaction of the diamine compound having a phosphorylcholine group represented by Formula (I) with the functional group-terminated prepolymer.

9. The process according to claim 6, wherein, at least on other diamine compound having no phosphorylcholine group is co-present in the polycondensation or polyaddition reaction of the diamine compound having a phosphoryleholine group represented by Formula (I) with another polymerizable monomer, or at least on other diamine compound having no phosphorylcholine group is co-present in the reaction of the diamine compound having a phosphorylcholine group represented by Formula (I) with the functional group-terminated prepolymer.

* * * * *

UNITED STATES PATENT AND TRADEMARK OFFICE
CERTIFICATE OF CORRECTION

| | | |
|---|---|---|
| PATENT NO. | : 8,063,238 B2 | Page 1 of 1 |
| APPLICATION NO. | : 12/439192 | |
| DATED | : November 22, 2011 | |
| INVENTOR(S) | : Yu Nagase et al. | |

It is certified that error appears in the above-identified patent and that said Letters Patent is hereby corrected as shown below:

Column 40, Line 65, Claim 7, after "one" insert -- other --

Column 40, Lines 65-66, Claim 7, delete "phosphoryleholine" and insert -- phosphorylcholine --

Column 42, Line 5, Claim 9, delete "on" and insert -- one --

Column 42, Line 8, Claim 9, delete "phosphoryleholine" and insert -- phosphorylcholine --

Column 42, Line 10, Claim 9, delete "on" and insert -- one --

Signed and Sealed this
Twenty-eighth Day of February, 2012

David J. Kappos
*Director of the United States Patent and Trademark Office*